United States Patent
Suzuki et al.

(10) Patent No.: US 6,942,615 B2
(45) Date of Patent: Sep. 13, 2005

(54) LIFE SUPPORT APPARATUS AND METHOD FOR PROVIDING ADVERTISEMENT INFORMATION

(75) Inventors: Takuji Suzuki, Yokohama (JP); Miwako Doi, Kawasaki (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 112 days.

(21) Appl. No.: 10/427,922

(22) Filed: May 2, 2003

(65) Prior Publication Data

US 2003/0204132 A1 Oct. 30, 2003

Related U.S. Application Data

(62) Division of application No. 09/866,828, filed on May 30, 2001, now Pat. No. 6,607,484.

(30) Foreign Application Priority Data

May 31, 2000 (JP) ........................................ 2000-163793

(51) Int. Cl.[7] ................................................ A61B 5/00
(52) U.S. Cl. ......................... 600/300; 705/10; 340/517; 128/920
(58) Field of Search ................................. 600/300–301, 600/529, 531; 128/903, 904, 920, 925, 924, 897; 705/2–4, 1, 10; 434/262, 235, 118; 340/573.1, 517; 342/457; 709/217; 455/66

(56) References Cited

U.S. PATENT DOCUMENTS 5,596,994 A * 1/1997 Bro ............................. 600/545
6,139,494 A * 10/2000 Cairnes ........................ 600/300
6,198,394 B1 * 3/2001 Jacobsen et al. .......... 340/573.1
6,241,684 B1 * 6/2001 Amano et al. ............... 600/531

FOREIGN PATENT DOCUMENTS

| JP | 7-124139 | 5/1995 |
| JP | 9-22314 | 1/1997 |
| JP | 10-71137 | 3/1998 |
| JP | 10-305016 | 11/1998 |

* cited by examiner

*Primary Examiner*—Mary Beth Jones
*Assistant Examiner*—Michael Astorino
(74) *Attorney, Agent, or Firm*—Finnegan, Henderson, Farabow, Garrett & Dunner, L.L.P.

(57) ABSTRACT

A life support apparatus comprising a vital information sensor attached to a body to acquire vital information of a user, a behavior information sensor attached to the body to acquire behavior information of the user, a situation recognition device which recognizes a user's situation based on the behavior information acquired by the behavior information sensor and the vital information acquired by the vital information sensor to generate user's situation information, a data base which stores stress management information are prepared in advance, an information search device which searches the data base for stress management information corresponding to the user's situation information, and an information presentation device which presents the stress management information obtained by the information search device to the user.

5 Claims, 17 Drawing Sheets

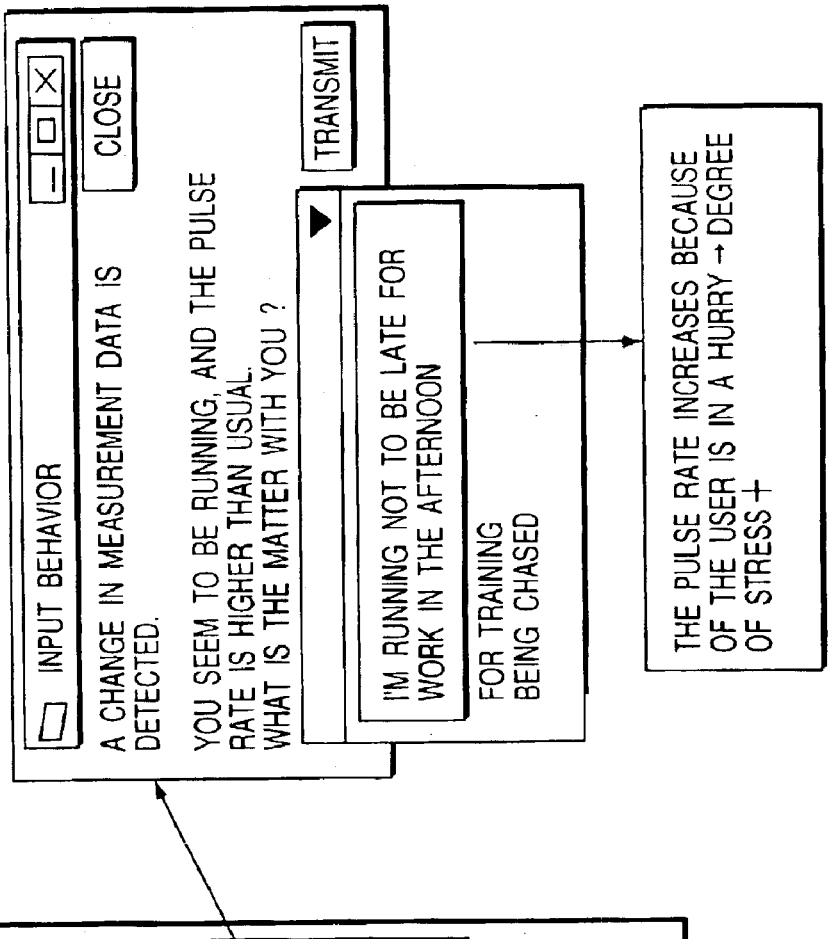
FIG. 7B
FIG. 7C
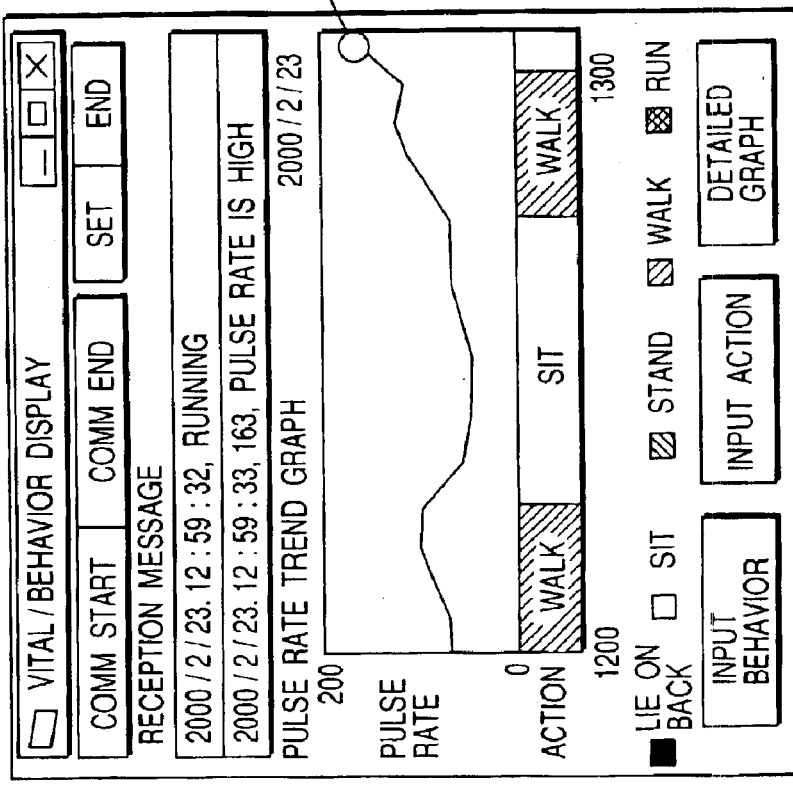
FIG. 7A

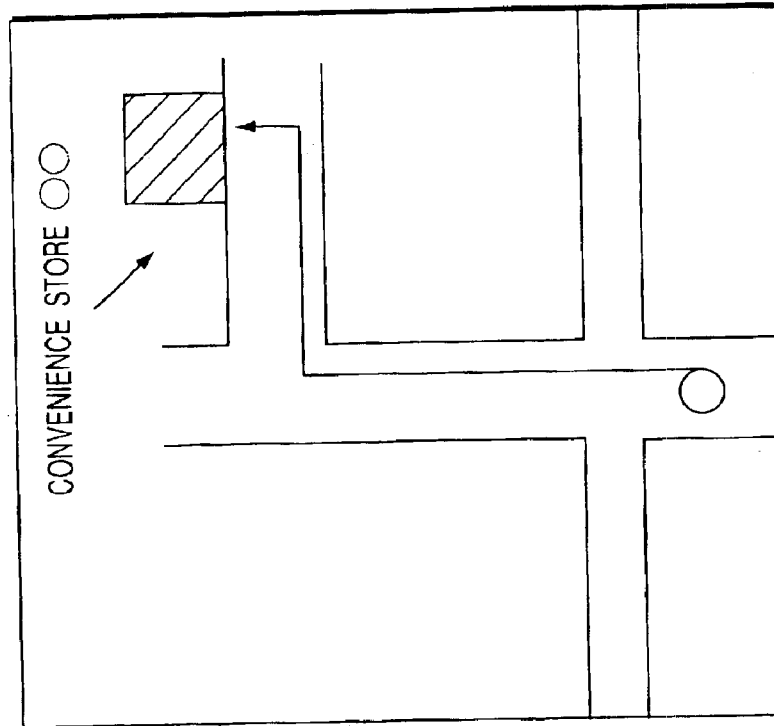
FIG. 10B
FIG. 10C
VOICE GUIDANCE
"CROSS THE FIRST INTERSECTION, TURN RIGHT AT THE NEXT INTERSECTION, GO STRAIGHT 20 M FROM THERE, AND YOU WILL FIND THE STORE ON YOUR LEFTHAND SIDE"
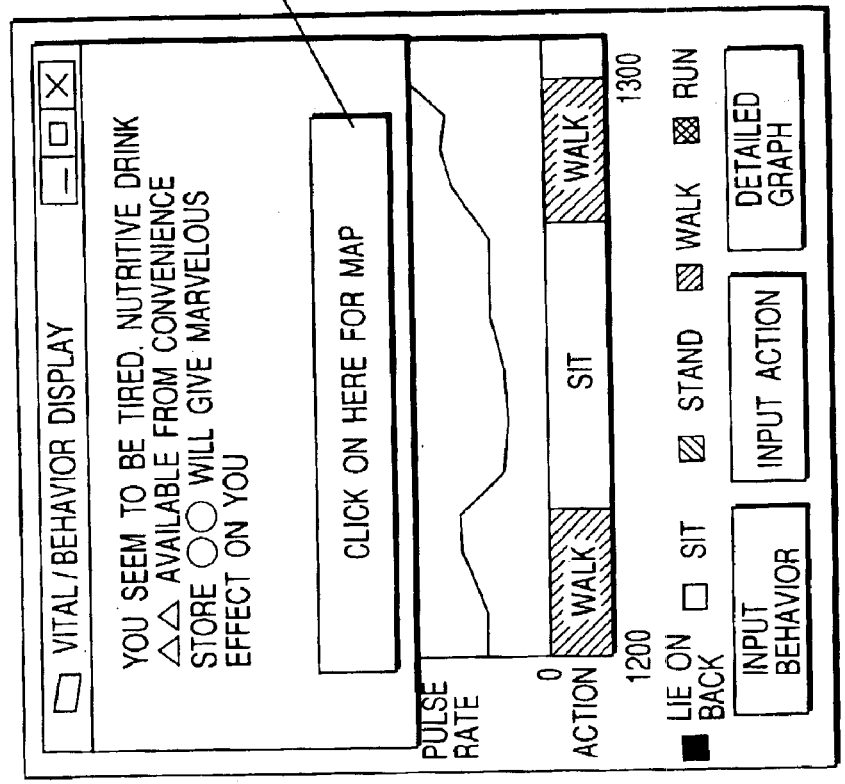
FIG. 10A

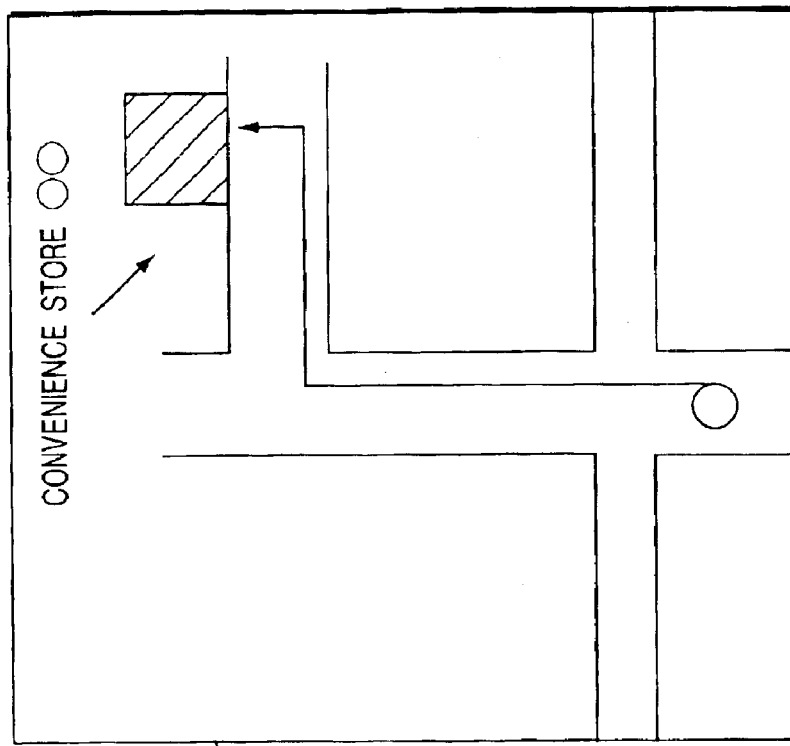
FIG. 11B
FIG. 11C
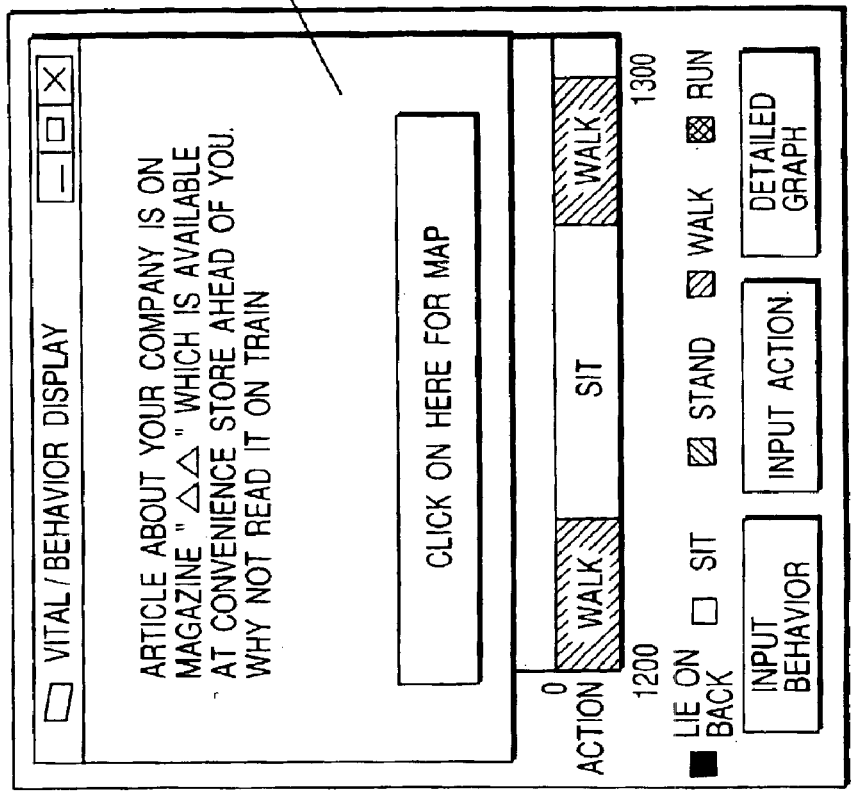
FIG. 11A

REGIONAL SENSOR INFORMATION CORPUS

A AREA (NEAR CONVENIENCE STORE ○○):

| SEASON | DAY OF WEEK | TIME | SEX | AGE | BEHAVIOR | EXPECTED BEHAVIOR | DEGREE OF STRESS | DEGREE OF FATIGUE |
|---|---|---|---|---|---|---|---|---|
| SUMMER | MONDAY | 8:00 | MALE | 35 | WALK (TO OFFICE) | GET TRAIN (TO OFFICE) | 60 | 50 |
|  |  | 8:01 | FEMALE | 18 | WALK (TO SCHOOL) | SIT DOWN (LESSON) | 40 | 30 |
|  |  | · | · | · | · | · | · | · |
|  |  | · | · | · | · | · | · | · |
| AUTUMN |  |  |  |  |  |  |  |  |
|  | SUNDAY |  |  |  |  |  |  |  |

FIG. 12

| PERSON TO MEET | ADDRESS | TEL | ... | DEGREE OF STRESS |
|---|---|---|---|---|
| ×○ ○○ | ○●-KU, ○○-SHI... | 012-345-6789 | | 60 |
| ○KO △△ | ○○-KU... | 03-3333-3333 | | 80 |
| .. | | | | |
| | | | | |
| | | | | |

FIG. 14

| SEASON | DAY OF WEEK | TIME | SCHEDULE / TASK (To/Do) | CONTENTS / VOLUME | ... | DEGREE OF STRESS | DEGREE OF FATIGUE |
|---|---|---|---|---|---|---|---|
| SUMMER | MONDAY | 20:00-22:00 | PAPER WRITING | A4:10 PAGES | | 60 | 50 |
| | | 17:00-17:30 | OFFICIAL TRIP REPORT | A4:1 PAGE | | 80 | 40 |
| | WEDNESDAY | 15:00-17:00 | ORDINARY MEETING | PROGRESS REPORT | | 90 | 70 |
| | .. | .. | .. | .. | | .. | .. |
| | | | | | | | |
| AUTUMN | SUNDAY | | | | | | |
| | | | | | | | |

| SENDER ID | SENDER NAME | ANSWER PERMISSION | ALLOWABLE RANGE ||||
|---|---|---|---|---|---|---|
| | | | LOCATION | BEHAVIOR | EXPECTED BEHAVIOR | DEGREE OF FATIGUE |
| 0001 | ○○ ○KI | INHIBIT | — | — | — | — |
| 0002 | ○KO △MOTO | PERMIT | PERMIT | PERMIT | PERMIT | <70 |
| ·· | ·· | ·· | ·· | ·· | ·· | ·· |

FIG. 19

| LOCATION | BAHAVIOR | INCOMING TELEPHONE CALL NOTIFICATION | MESSAGE DISPLAY |
|---|---|---|---|
| OUTDOOR | WALK | VOICE | VOICE |
| IN TRAIN | STAND | VIBRATION | TEXT ON WRIST WATCH |
| | SIT | VIBRATION | TEXT ON DISPLAY |
| INDOOR | — | VIBRATION | |
| ·· | ·· | | |

LIFE SUPPORT APPARATUS AND METHOD FOR PROVIDING ADVERTISEMENT INFORMATION

This is a division of application Ser. No. 09/866,828, filed May 30, 2001 now U.S. Pat. No. 6,607,484, which is incorporated herein by reference.

CROSS-REFERENCE TO RELATED APPLICATIONS

This application is based upon and claims the benefit of priority from the prior Japanese Patent Application No. 2000-163793, filed May 31, 2000, the entire contents of which are incorporated herein by reference.

BACKGROUND OF THE INVENTION

1. Field of the Invention

The present invention relates to a wearable type life support apparatus for measuring and determining various states of a user by using a wearable device and giving life support by an information service such as medical administration or personal navigation according to the user's situation, a life support method, and an advertisement providing method.

2. Description of the Related Art

As the society becomes complex, stress in daily life is said to be one factor of various problems of the modern society because stress adversely affects the health of people by, e.g., causing life-style related diseases such as heart diseases or mental diseases such as depression, and also triggers crimes.

"Stress" originally means stimuli from the external world (Yoshinosuke Tadai, "What is Stress?", Kodansha Bluebacks). Currently, "stress" is taken to also include adaptive reaction against stress. When the adaptive reaction exceeds human limitations, various diseases or mental disorders are said to occur. Alternatively, these disorders occur presumably when the sympathetic nerve and the parasympathetic nerve become unbalanced due to a change in rhythm of life.

How to cope with stress is important for the people of this day. The best measure against stress is stress control, i.e., to eliminate stress. Various methods are recommended to this end: "to see or listen to images or music that prompts relaxation", "to do anything one likes", and "to shout loudly".

However, a person who is pressed with business every day is often unconscious of the buildup of stress. He/she is heavily fatigued, and in the worst case, comes to a sudden death. It is therefore important to realize and control stress before it becomes serious or prevent stress from building up.

As the importance of measures against stress is recognized, development of apparatuses for acquiring vital information of a user and measuring and managing user's stress is an urgent necessity. Several apparatuses have already been proposed.

However, since a person experiences stress in a variety of situations in daily life, the vital information to be measured largely changes depending on external situations such as the peripheral environment and the position of the person as well as internal situations such as action and mental condition. For this reason, it is difficult to accurately grasp user's stress state unless the vital information is analyzed and determined in association with user's behavior.

To make the user realize stress, he/she must be notified when or immediately after stress builds up. Otherwise, the user cannot be aware of stress, and if the user is unaware of the stress, life style and the like can hardly be improved.

Hence, demand has arisen for the development of a system which can determine the stress situation in daily life and notify a user of it so as to assist stress control.

For stress control, it is important in terms of care to provide the user an optimum measure to cope with the situation. However, such a technique is still absent.

For portable type information communication devices such as handyphones, ringing tones or conversing voice at a public place as in a train poses a problem. To solve this problem, a technique of setting a vibrator call mode as a "manner" mode or receiving a message by an automatic answering telephone function is already widely used. However, since urgent contact is sometimes required, a mechanism capable of easily communicating a situation or message without voice communication is required.

In the world of the Internet, advertisement display (banner advertisement) according to the Internet use situation of a user, such as Internet advertisement, is widely used. However, information providing according to each scene of user's daily life and business that uses the information providing service for advertisement have not been realized yet.

It is an object of the present invention to provide a life support apparatus and method which can determine the stress situation in daily life and notify a user of it to cause the user to realize the stress or can support the user of a method of eliminating stress or care against the factor that has caused the stress, on the basis of the situation of the user.

BRIEF SUMMARY OF THE INVENTION

The present invention provides a system which can grasp the situation of a user by various sensors, grasp the degree of stress corresponding to each situation, and offers a service such as occasional life style improvement or relaxation using the concept of a wearable computer always attached to the user. In addition, the system is applied to consumer marketing or advertisement display business.

According to a first aspect of the present invention, there is provided a life support apparatus comprising a vital information sensor attached to a body to acquire vital information of a user, a behavior information sensor attached to the body to acquire behavior information of the user, a situation recognition device which recognizes a user's situation based on the behavior information acquired by the behavior information sensor and the vital information acquired by the vital information sensor to generate user's situation information, a data base which stores stress management information are prepared in advance, an information search device which searches the data base for stress management information corresponding to the user's situation information, and an information presentation device which presents the stress management information obtained by the information search device to the user.

According to this arrangement, the vital information and behavior information of the user are acquired, the user's situation is recognized on the basis of the acquired behavior information, corresponding information is obtained from pieces of information for dealing with stress, which are prepared in advance, using the acquired user's situation information as a key, and the obtained information is presented to the user.

The stress situation is determined in daily life, and optimum service information for stress elimination or care is provided to the user in accordance with the situation, thereby enabling life advice contributing to user's healthcare.

According to a second aspect of the present invention, there is provided a life support apparatus comprising a user information sensor attached to a body to acquire information representing a user's situation, a situation recognition device which recognizes the user's situation based on user information acquired by the user information sensor, a transceiver device which transmits the information of the user's situation recognized by the situation recognition device and receive external information transmitted from an external apparatus, and a presentation device which presents the external information received by the transceiver device to the user, the external information including an advertisement appropriate for the user, which is sent from the external apparatus in correspondence with the user's situation information.

According to this arrangement, information representing the physical situation of the user is acquired, the user's situation is recognized on the basis of the acquired information, and advertisement information corresponding to the information of the recognized user's situation can be obtained from the server that hold various kinds of advertisement information corresponding to physical situations and presented to the user.

The stress situation is determined in daily life, optimum service information for stress elimination or care is provided to the user in accordance with the situation in consideration of the time and circumstances, and the user is prompted to use the service, thereby enabling life advice contributing to the commercial effect and user's healthcare.

According to a third aspect of the present invention, there is provided a life support apparatus comprising various kinds of information presentation media for a voice or text message, a user information sensor attached to a body to acquire user information representing a user's situation, a situation recognition device which recognizes the user's situation based on user information acquired by the user information sensor to generate user's situation information, a communication device connected to the situation recognition device and communicating with external equipment, a situation information conversion device which selects an optimum message presentation medium from the information presentation media in accordance with the user's situation information and convert the situation information into a form corresponding to the optimum message presentation medium, to present call message information sent from the message sender and received by the communication device to the user, and an answer transmission device which transmits the user's situation information converted by the situation information conversion device to the message sender.

In this arrangement, upon reception of incoming message information addressed to the user, the call message is converted into a form that uses an appropriate medium corresponding to the user's situation recognized by the situation recognition device, and presented. The answer transmission device transmits the user's situation information converted by the situation information conversion device to the message sender.

The user's current situation is determined in daily life to cope with an incoming call in accordance with the user's situation at that time in consideration of specific time and circumstances such that the user need not worry about it, thereby enabling life advice without imposing any stress on the user.

According to a fourth aspect of the present invention, there is provided an advertisement information providing method comprising preparing a server which holds various kinds of advertisement information corresponding to physical situations, and extracting optimum advertisement information corresponding to a situation of a user to present the optimum advertisement information to the user.

According to the present invention, the server which hold various kinds of advertisement information corresponding to physical situations is prepared, the physical situation of the user is detected, and optimum advertisement information is obtained from the server in correspondence with the user's situation and presented to the user.

The user's current situation is determined in daily life, and advertisement information such as optimum merchandise to deal with stress can be presented to the user on the basis of the determination result in consideration of the user's situation at that time. This contributes to user's stress care and healthcare, and commercially effective advertisements can be provided.

BRIEF DESCRIPTION OF THE SEVERAL VIEWS OF THE DRAWING

FIG. 5 is a view for explaining the structure of a reference sensor information corpus related to stress, which is used in the embodiment of the present invention;

FIGS. 7A, 7B, and 7C are views for explaining behavior-related pulse rate trend graph display and a behavior input window for an abnormal value, which are used in the embodiment of the present invention;

FIGS. 10A, 10B, and 10C are views for explaining advertisement display corresponding to the degree of user's fatigue/stress and a road map window, which are used in the embodiment of the present invention;

FIGS. 11A, 11B, and 11C are views for explaining advertisement displays corresponding to the behavior information of the user and a road map, which are used in the second embodiment of the present invention;

FIG. 12 is a view for explaining the structure of a regional sensor information corpus related to stress, which is used in the embodiment of the present invention;

FIG. 14 is a view showing the structure of address book data including degree-of-stress information, which is used in the embodiment of the present invention;

FIG. 15 is a view for explaining the structure of a relational database of a schedule/task list, the degree of stress, and the degree of fatigue, which is used in the embodiment of the present invention;

FIG. 18 is a view showing an allowable range setting table of answer contents for each message sender, which is used in the embodiment of the present invention;

FIG. 19 is a view showing an answer device setting table for each user's situation, which is used in the embodiment of the present invention.

DETAILED DESCRIPTION OF THE INVENTION

The embodiments of the present invention will be described below in detail with reference to the accompanying drawing.

(First Embodiment)

A wearable type life support apparatus which can give a life advice effectively used for healthcare and medical administration by monitoring stress applied on the body of a user, and when stress occurs, relaxing the stress to suppress mental and physical damage by the stress, and can also give navigation by utilizing the stress to improve the ability of the user will be described here with reference to FIG. 1.

Figure 1:
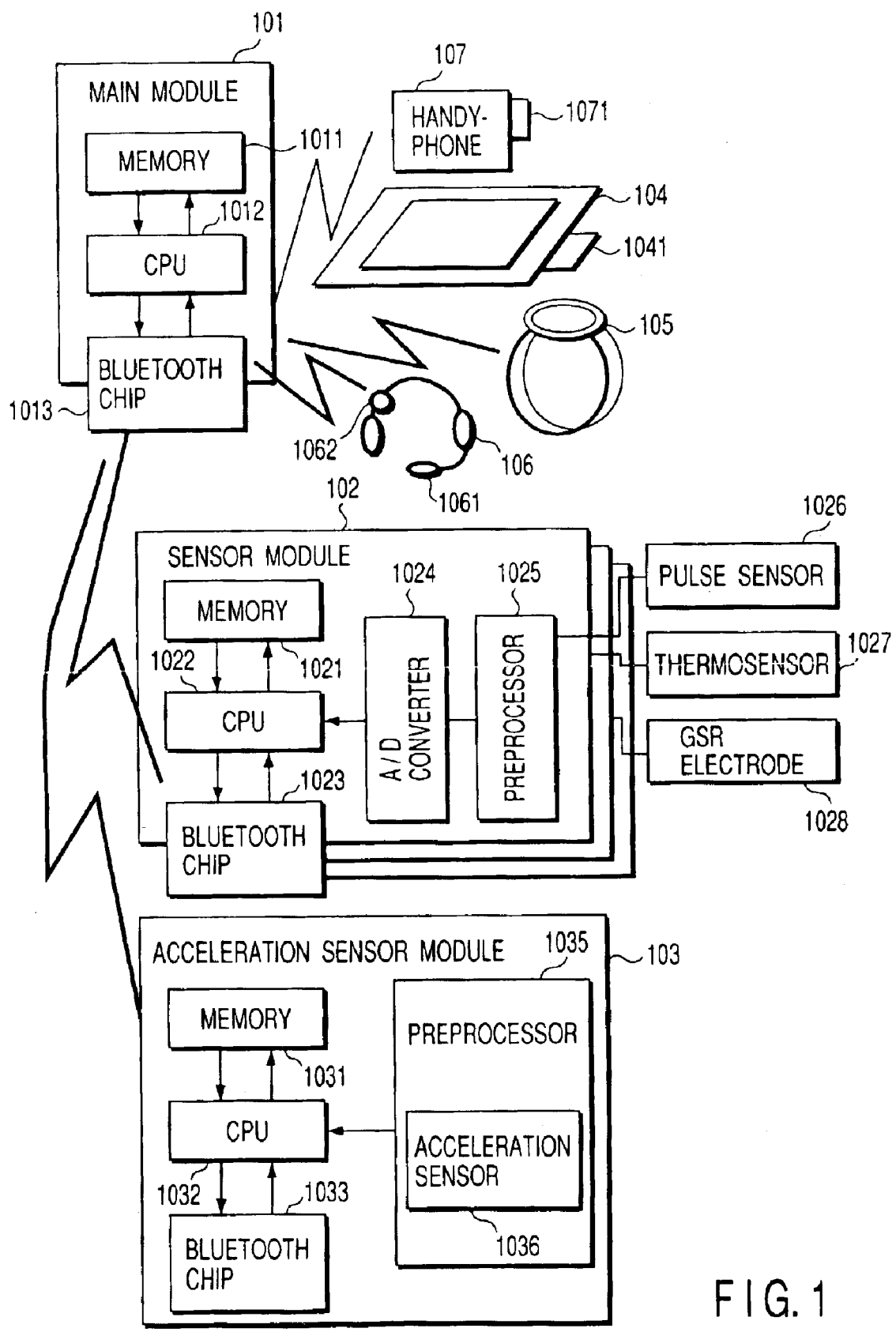
FIG. 1 is a schematic block diagram showing a wearable type life support apparatus according to the first embodiment of the present invention.

The wearable type life support apparatus shown in FIG. 1 has a main module 101, a sensor modules 102, an acceleration sensor module 103, a display 104, a wrist watch type display 105, a headset 106, and a handyphone 107.

Of these components, the main module 101 is a compact and lightweight computer such as a wearable computer, which has a function of analyzing collected vital information to grasp the degree of stress and providing various kinds of supports in accordance with the degree of stress. The main module 101 also has functions of processing collected data, sending the processed data to the database of a center, executing desired processing using information obtained from the database, and transmitting/receiving information or a control command to/from the headset 106, display 104, or handyphone 107.

The main module 101 is formed from a memory 1011 and CPU 1012. Application programs and control programs for implementing the above-described functions and an OS (Operating System) as the basic software of the computer are stored in the memory 1011. The CPU 1012 executes these programs to realize various desired processing operations. The main module 101 also has a calendar/timepiece function such that collected or processed information can be managed with a time stamp.

The main module 101 also has, e.g., a function of synthesizing a character string prepared as text data into a voice and outputting a voice signal, a function of recognizing a voice signal and converting it into text data, and a function of collating data. The main module 101 has, e.g., a Bluetooth chip 1013 for executing communication between modules using Bluetooth as an international standard short-distance radio communication device which has received a great deal of attention in recent years. The main module 101 can store data to be handled in the system, systematically manage the entire system, execute data communication between the modules, and communicate with a home server and management server (not shown).

The sensor modules 102 collect and transmit vital signals and are connected to vital signal detection sensors such as a pulse sensor 1026 for detecting pulses of a human body, a thermo sensor 1027 for detecting the body temperature of the human body, and a GSR (Galvanic Skin Reflex) electrode 1028 for detecting the skin resistance of the human body. Each sensor module 102 comprises a preprocessor 1025 that amplifies and preprocesses the detection signal from each sensor, an A/D converter 1024 that converts the sensor detection signal preprocessed by the preprocessor 1025 into digital data, a CPU 1022 that executes various control operations and data processing, and a memory 1021. Each sensor module 102 also incorporates a Bluetooth chip 1023 to execute data communication with the main module 101.

The structures from the sensors 1026, 1027, and 1028 to the sensor modules 102 are divided for the respective sensors. However, the structures for the respective sensors may be integrated into a single sensor module 102. Processing operations in each sensor and module 102 may be integrated. A microcontroller (e.g., PIC16F877 available from MicroChip Technologies) incorporating an A/D conversion function may be used as the CPU 1022 without preparing a separate A/D converter.

The preprocessor 1025 not only amplifies the signal detected by each sensor by an appropriate gain but also incorporates a filter circuit that performs high-pass filter processing depending on the type of signal or low-pass filter (anti-aliasing filter) processing in accordance with the band of each signal. Each sensor has a plurality of channels as needed.

The handyphone 107 is a normal handyphone having a liquid crystal display panel, a plurality of operation buttons 1071 including dial keys, and a transceiver and inputs/outputs a voice. The handyphone 107 also incorporates a Bluetooth chip and can communicate with the main module 101. With this arrangement, voice input/output and cursor control by cursor keys can be performed.

The display 104 is a display terminal formed from a portable liquid crystal display panel which displays text data or an image and is exclusively construed for display. The display 104 has a Bluetooth chip 1041 and can control display contents upon receiving display data and the like from the main module 101 through the Bluetooth chips 1013 and 1041.

The headset 106 is an input/output terminal used on the user's head, i.e., a headset incorporating a Bluetooth chip and CCD camera (solid state image sensor 1062) as well as a headphone (or earphone) and microphone 1061. The headset 106 is a device for voice/image interface. The headset 106 also incorporates a Bluetooth chip to transmit and receive a voice signal and transmit an image. The headset 106 can be used simultaneously together with the handyphone 107.

The wrist watch type display 105 is a liquid crystal display panel having a wrist watch shape used on the user's arm. The wrist watch type display 105 incorporates a Bluetooth chip to transmit/receive data or command to/from the main module 101.

This apparatus assumes digital communication by Bluetooth. However, a radio communication device of any other scheme or a scheme of performing D/A conversion and transferring a voice signal to the headphone by FM modulation may be employed. A voice signal may be transferred not by radio communication but by cable connection. An image may be acquired by a digital camera attached independently of the headset 106.

The function of the system with the above arrangement will be described next.

Figure 2:
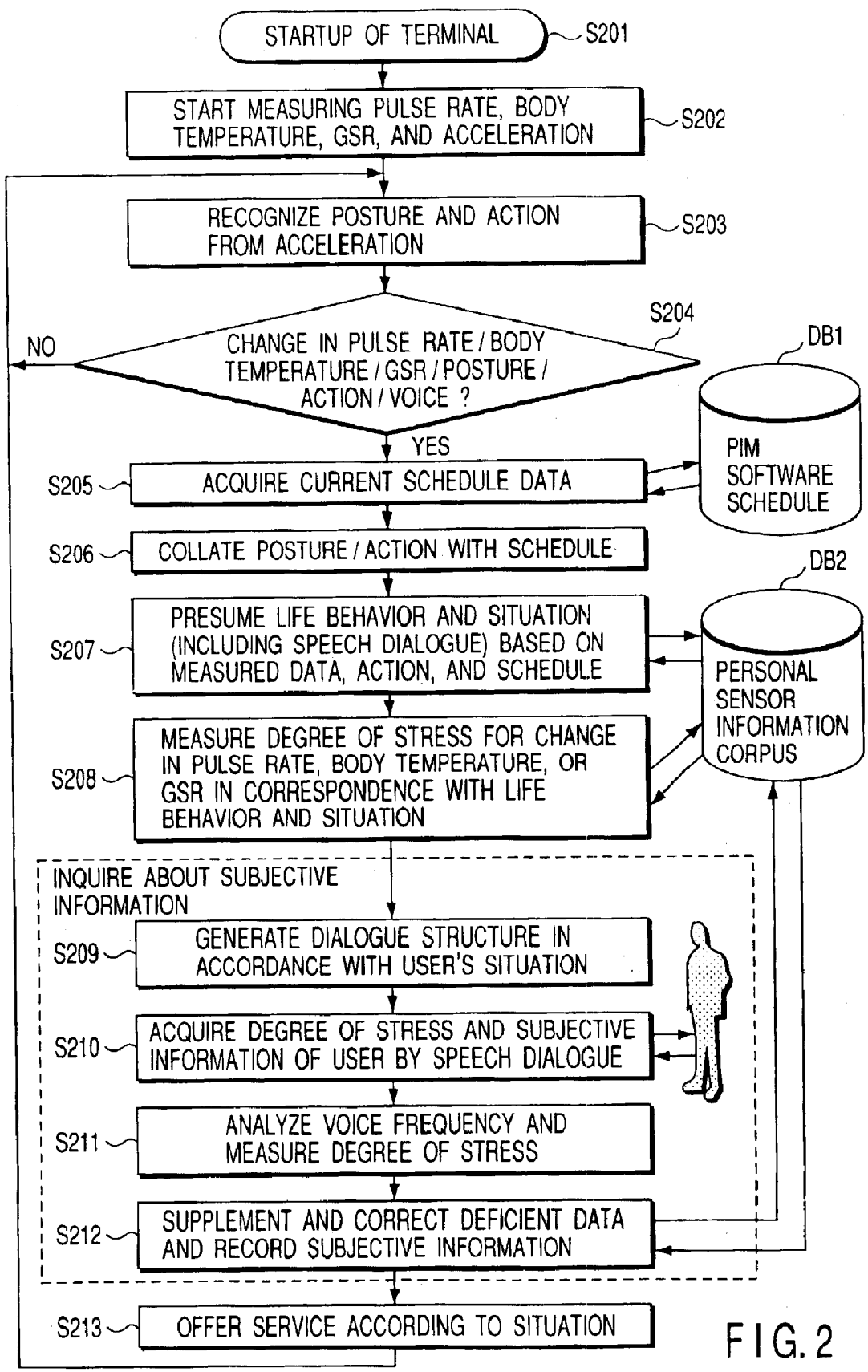
FIG. 2 is a flow chart showing the processing procedure of the wearable type life support apparatus according to the first embodiment of the present invention.

FIG. 2 is a flow chart showing the flow of operation of the system according to the present invention having the arrangement shown in FIG. 1. The operation will be described with reference to the flow chart show in FIG. 2. The user carries the main module 101, sensor modules 102, handyphone 107, display 104, and headset 106. The pulse sensor 1026, thermosensor 1027, GSR electrode 1028, and acceleration sensor 1036 are set on the user, and then, the system is activated to start operation (step S201 in FIG. 2).

When the sensors are set and activated, they start to detect a vital signal. As a result, a pulse rate detection signal by the pulse sensor 1026, a temperature detection signal by the thermosensor 1027, a galvanic skin reflex detection signal by the GSR electrode 1028, and an acceleration measurement signal by the acceleration sensor 1036 are obtained (step S202 in FIG. 2). The measurements are done continuously, periodically (every minute, every 10 minutes, or the like), or in accordance with a measurement instruction from the main module 101 or a user's instruction.

The analog detection signals obtained by the sensors 1026, 1027, and 1028 are amplified, filtered, and A/D-converted by the sensor modules 102. The A/D-converted data are transferred to the main module 101 through a short-distance radio device such as the Bluetooth chip 1023.

The main module 101 processes the measurement data by a preset logic, thereby determining the user's situation.

First, the main module 101 recognizes the action (behavior) or posture of the user on the basis of acceleration information obtained from the acceleration sensor 1036 (step S203 in FIG. 2).

Figure 4:
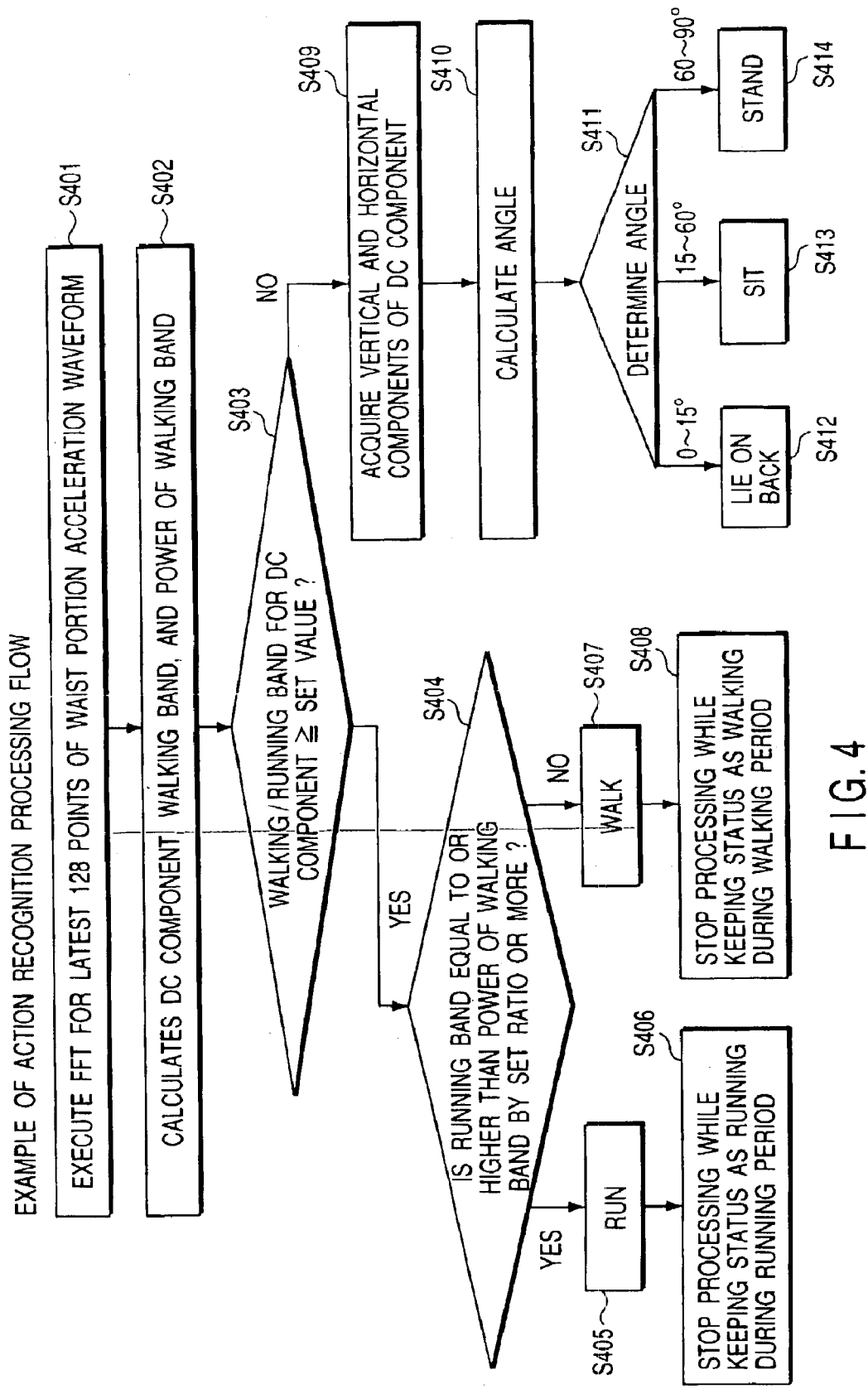
FIG. 4 is a flow chart showing action and posture recognition processing used in the embodiment of the present invention.

The action/posture recognition method in step S203 is shown in the action recognition flow chart of FIG. 4.

<Action/Posture Recognition in S203>

Referring to FIG. 4, the acceleration information is obtained by attaching, e.g., a three-dimensional acceleration sensor to a predetermined portion of the human body as the acceleration sensor 1036, thereby measuring the posture and action. The three-dimensional acceleration sensor 1036 can be formed by perpendicularly laying out two two-dimensional acceleration sensors such as "ADXL202JC" available from Analog Devices Corp. The three-dimensional acceleration sensor 1036 is attached to, e.g., the waist to measure the motion of the body center (trunk) portion.

Figure 3:
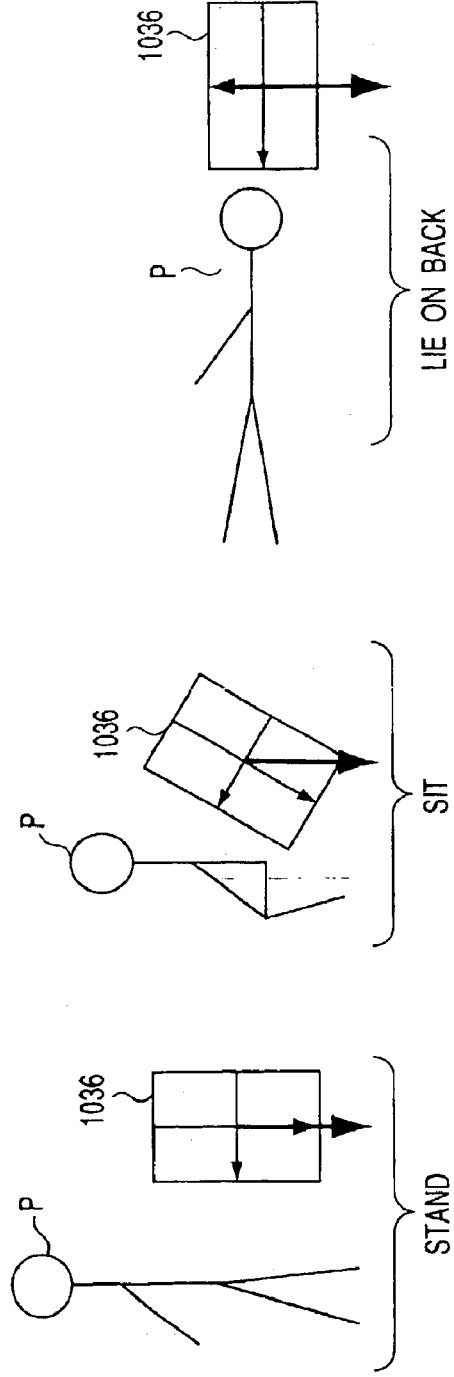
FIGS. 3A to 3C are schematic views showing the principle of human posture recognition used in the present invention.

As shown in FIGS. 3A, 3B, or 3C, the tilt of the sensor is obtained from a DC component, i.e., an output obtained by passing the acceleration waveform from the acceleration sensor 1036 through a low-pass filter, thereby detecting the posture.

For example, the sensor 1036 is attached to the joint portion of the base of the femoral region of a user P. An angle is obtained from the vertical and horizontal components of the DC component, and the posture can be recognized on the basis of the angle: when the sensor is almost horizontal, the user is lying on his/her back (FIG. 3C) or on his/her face, when the sensor is almost vertical, the user stands upright (FIG. 3A), and the sensor has an angle therebetween, the user is sitting (FIG. 3B).

The action (walking, running, bicycle, car, train, or the like) can be identified from the frequency component and variation pattern of an AC component. For example, the fundamental frequency of walking is 60 to 100 (times/min), and that of running is 120 to 180 (times/min). Hence, the fundamental frequency component is acquired by performing frequency analysis (FFT (Fast Fourier Transform)) for the detected signal (S401 in FIG. 4) or by detecting waveform peaks and peak interval. The powers in the respective bands are compared, thereby recognizing walking or running.

If the acceleration sensor 1036 is attached not to the waist but to a leg portion, e.g., the femoral region of a leg, the acceleration during walking is maximized by vibration when the foot touches the ground. However, during running (running fast), the acceleration is maximized by vertical movement of the waist when the feet touch the ground. For this reason, for walking, the fundamental frequency must be further halved. Alternatively, since the vertical amplitude for running is larger by twice or more than that for walking, the amplitude values at the time of peak detection are compared, thereby recognizing walking or running.

The above methods may be combined, or either method may be used.

According to FIG. 4, FFT is executed for latest 128 points of waist portion acceleration waveform (S401). DC component, walking band, and power of walking band are calculated (S402). It is determined that walking/running band for DC component≧set value (S403). If the determination is YES, it is determined whether the running band is equal to or higher than the power of walking band set ratio or more (S404). If this determination is YES, run is performed (S405). The processing is stopped while keeping status as running during the running period (S406). If the determination is NO, walk is performed (S407). The processing is stopped while keeping status as walking during a walking period (S408). If the determination of step S403 is NO, vertical and horizontal components of DC component are acquired (S409), and an angle is calculated (S410). The angle is determined as 0°–15°, 15°–60° or 60°–90° (S411). The angle of 0°–15° is determined as lie on back (S412), the angle of 15°–60° is determined as sit (S413), and the angle of 60°–90° is determined as stand (S414).

Figure 17:
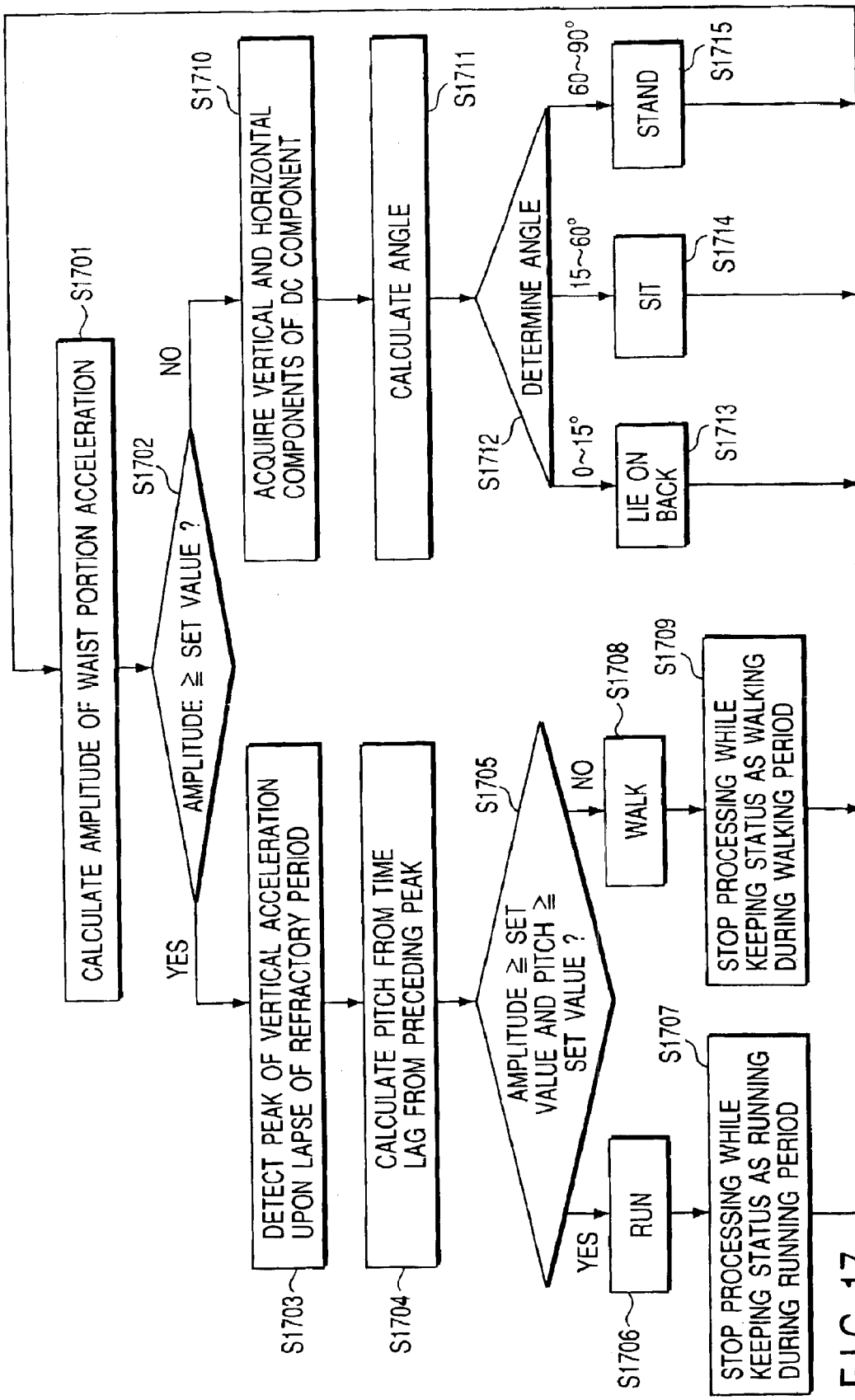
FIG. 17 is a flow chart of posture/action recognition based on peak detection of a waveform as a function of time, which is used in the embodiment of the present invention.

In the flow chart shown in FIG. 4, FFT is used for analysis processing. However, the present invention is not limited to this. Another spectrum analysis device such as wavelet transformation may be used. Alternatively, pattern matching between the waveforms of fundamental frequencies may be performed to recognize "running", "walking", "ascending stairs", or "descending stairs". Simple peak detection may be performed, and the number of steps may be measured from the period. Alternatively, as shown in FIG. 17, peak detection may be performed along the time axis to obtain the walking or running pitch. In other words, the amplitude of a waist portion acceleration is calculated (S1701). It is determined whether the amplitude≧set value (S1702). If the determination is YES, the peak of a vertical acceleration is detected upon lapse of a refractory period (S1703). A pitch is calculated from a time lag from a preceding peak (S1704). It is determined whether the amplitude a set≧value and the pitch≧a set value (S1705). If the determination is YES, run is performed (S1706). The processing is stopped while keeping the status as running during a running period (1707). If the determination is NO, a walk is carried out (S1708). The processing is stopped while keeping the status as walking during a walking period.

If the determination of step S1702 is NO, vertical and horizontal components of DC component are acquired (S1710), and an angle is calculated (S1711). The angle is determined as 0°–15°, 15°–60° or 60°–90° (S1712). The angle of 0°–15° is determined as lie on back (S1713), the angle of 15°–60° is determined as sit (S1714), and the angle of 60°–90° is determined as stand (S1715).

Posture/action recognition is done by the main module 101. However, posture/action recognition may be done by the sensor modules 102, and resultant status data (posture and action) may be transmitted periodically or when a change occurs.

To recognize a position indoors, the main module 101 communicates with a radio tag (e.g., a Bluetooth chip) prepared in each room to detect the location. Outdoors, a position information service of a handyphone (or PHS) or a GPS (not shown) is used to detect the location.

With the above operation, action (behavior) of the user can be recognized from the acceleration information. When the above processing is ended, the flow advances to determination processing in step S204.

The determination processing in step S204 is executed to check whether the pulse rate, body temperature, GSR (Galvanic Skin Reflex), posture, action, or voice has changed. If NO in step S204, the flow returns to step S203 in FIG. 2. If YES in step S204, the flow advances to processing in step S205.

For the determination processing in step S204, the pieces of information of the pulse rate, body temperature, GSR, posture, action, or voice are necessary. Of these pieces of information, pieces of vital information such as the pulse rate, body temperature, and GSR are measured simultaneously with the above-described user's behavior state detection. The measuring method will be described below.

<Vital Information Measurement>

The pulse rate is obtained by the pulse sensor 1026. The pulse sensor 1026 detects a pulse by photoelectrically sensing a change in bloodstream through peripheral blood vessels in, e.g., a finger, wrist, or ear as a part to be measured. A portion where blood vessels concentrate is irradiated with light using, as a light source, an incandescent lamp or LED (Light Emitting Diode) capable of emitting light having an absorption wavelength of hemoglobin contained in blood in a large quantity. The transmitted or reflected light is received by a photodiode as a photoelectric element, photoelectrically converted, and measured.

A potential waveform on which the influence of light absorption by hemoglobin that flows in the bloodstream is obtained as a detection signal from the component, e.g., photodiode of the pulse sensor 1026. This signal is amplified by the preprocessor 1025, filtered, converted into digital data by the A/D converter 1024, transmitted from the sensor module 102 through the Bluetooth chip 1023, and thus received by the main module 101 as potential waveform data as pulse rate data.

The main module 101 analyzes the peak interval or frequency of the potential waveform of the received pulse data and calculates the pulse rate from the peak frequency. The analysis and calculation are done by the CPU 1012.

The pulse sensor 1026 can have the shape of an earring, ring, or wrist watch, and any shape can be employed. Alternatively, the pulse sensor 1026 may be incorporated in the headset 106 shown in FIG. 1 such that the light emitting diode (incardescent lamp or LED) and photoelectric element (photodiode) or CdS cell are arranged on the front and rear sides of an earlobe. The light emitting and photoelectric elements may be incorporated in a ring or wrist watch, and the sensor may be incorporated in each module.

When, e.g., two pulse sensors 1026 are set at a predetermined interval to measure two waveforms, the resultant digital signals are received by the main module 101, the blood pressure or the elastic modulus of blood vessels can be obtained from the difference between the waveforms.

In addition, when LEDs for two wavelengths, i.e., absorption wavelength of oxyhemoglobin and that of reduced hemoglobin are used to irradiate blood vessels with light, and reflected light is measured, the oxygen saturation in the artery can be calculated.

Alternatively, when blood vessels are irradiated with light from an LED having an absorption wavelength of glucose, the blood sugar value can be measured using the reflected light.

In measuring the pulse rate, the heartbeat rate may be calculated using an electrocardiogram on the basis of the peak interval or peak frequency obtained from frequency analysis (this method is medically stricter).

The pulse rate value, blood pressure value, and blood sugar value are always measured and stored in the memory 1011 of the main module 101. Alternatively, measurements are performed periodically or at an arbitrary time in accordance with an instruction from the main module 101 to store data.

To measure the body temperature, the thermosensor 1027 is used. The thermosensor 1027 is formed from a detection device such as a thermocoupler or thermistor. The detection device is brought into contact with the body surface of the user, and the output from the detection device is converted into a temperature in accordance with the characteristics of the sensor.

To measure the GSR, a pair of electrodes are attached to the body surface of the user at a predetermined interval, a weak current is supplied across the electrodes, the potential difference and current value are measured, and the resistance value is calculated using the measurement values. In the measurement, drift components are removed from a waveform corresponding to the measurement result obtained from the two electrodes, and then, the amplitude of the leading edge and the number of leading edges are acquired. The drift components are acquired from the average value of the waveform.

These data are also converted into digital data, transmitted to the main module 101 by radio, and stored in the memory 1011 of the main module 101, like the output from the pulse sensor 1026.

Together with these measurement values, analog (voltage) data from the acceleration sensor 1036 is also A/D-converted and stored in the memory 1011. These data are linked with each other by giving measurement times to the respective data or recording the data in the same record.

The pieces of vital information are obtained in this way. If the vital information or posture, action, or voice information changes, the CPU 1012 of the main module 101 acquires current schedule data by processing in step S205.

The presence/absence of a change in vital information or posture or action information is determined on the basis of the following reference.

In the measurements continued in the above-described manner, a change means that the vital information (pulse rate, body temperature, or GSR) abruptly changes or becomes abnormal (for example, the pulse rate is "120" or more, or the body temperature is "37° C." or more), or the action information represents a status change such as "the user stops walking". When such a change is detected (step S204 in FIG. 2), the CPU 1012 of the main module 101 acquires schedule data including the change time by, e.g., PIM (Personal Information Manager) software that belongs and is compatible to the OS of the main module 101 (by, e.g., application "Microsoft Outlook 2000" if the OS (Operating System) of the main module 101 is "Windows" available from Microsoft) (step S205 in FIG. 2).

Consistency between the pieces of information and the schedule is checked (step S206 in FIG. 2), and any inconsistencies and deficient information are acquired from the user by speech dialogue and supplemented (step S207 in FIG. 2).

The method of acquiring and supplementing information from the user by speech dialogue will be described below.

Assume that the absolute values of the AC component outputs from the acceleration sensor 1036 in the three axial directions (x-axis, y-axis, and z-axis) fall outside a preset range. The CPU 1012 of the main module 101 determines that "the user is acting" because the absolute values of the AC components in the three axial directions exceed the set value, and asks the user "What are you doing now?" and executes voice recognition for the answer, thereby inputting behavior information.

More specifically, text data "What are you doing now?" is prepared as question data, and this data is synthesized into a voice signal and transmitted to the headset 106 through the Bluetooth chip 1013.

The headset 106 receives the voice signal through the Bluetooth chip of its own, transfers the voice signal to the headphone, and causes it to output voice. The user who is wearing the headset 106 can hear the question from the main module 101, "What are you doing now?"

The user answers this question with his/her current situation by speaking. For example, "ascending stairs" or "standing up from a chair" The user's voice is converted into a voice signal by a microphone 1061 of the headset 106, and the headset 106 transmits the voice signal through the Bluetooth chip of its own by radio. The main module 101 of the user receives, through the Bluetooth chip 1013, the voice signal transmitted by radio. The CPU 1012 of the main module 101 executes voice recognition processing for the voice signal and grasps the contents.

Using the PIM software, the CPU 1012 of the main module 101 acquires, from a database DB1, the user's current schedule data managed by the software (step S205 in FIG. 2). The schedule is prepared in advance in accordance with the behavior plan of the user by specifically setting dates, times, and contents.

The CPU 1012 of the main module 101 collates the behavior data recognized from the acceleration with the schedule data (step S206 in FIG. 2). If the collation fails, a dialogue for checking it may be done to correct the expectation result on the basis of the result of dialogue. Conversely, when the user is standing still for a long time, it is checked by collating the schedule whether the behavior has no problem. If the collation fails, the CPU inquires of the user.

This inquiry is also done by, e.g., speech dialogue.

Collation with the schedule may be triggered by vital information. For example, when the pulse rate increases at the scheduled desk work time, the behavior possibly changes, and the CPU asks the user, e.g., "Are you walking or running?" If it is determined as a result of check that the user is at desk working, the increase in pulse rate is supposed to be caused by a mental or morbid factor. The main module 101 asks the user "Are you feeling unwell?" through the headset 106 to check whether the user feels stress.

If no answer to this question is received from the user, the CPU 1012 of the main module 101 recognizes that the user's illness is serious. In this case, under the control of the CPU 1012, the main module 101 searches for medical information registered in advance, controls the handyphone 107 to execute dial call origination, and notifies the family physician of the emergency by, e.g., transmitting a voice message or a mail message prepared for emergency from the handyphone 107, or alarms those who are around the user.

The CPU 1012 of the main module 101 estimates the situation or life behavior on the basis of the measurement data, action, and schedule (step S207 in FIG. 2).

That is, the CPU searches a personal sensor information corpus DB2 in the terminal (main module 101) for sensor information with the same conditions on the basis of the obtained behavior information (where the user is and what the user is doing) and date/time data of the user, and compares the obtained sensor information with the measured sensor information to determine whether the value or change trend has a significant difference.

The CPU 1012 of the main module 101 measures the degree of stress from changes in pulse rate, body temperature, and GSR corresponding to the life behavior and situation (step S208 in FIG. 2).

In the main module 101, the standard range of each vital information is held in the memory 1011 as a parameter in correspondence with each behavior information, and each vital information is compared with the standard range. When the information to be measured falls within the standard range, the value is determined to be normal. When the information falls outside the standard range, the value is determined to be abnormal. Each parameter may be automatically set on the basis of data in normal state. Alternatively, the pattern (waveform) of a change in vital information for a certain behavior is stored, a correlation coefficient with respect to the pattern is acquired, and abnormality is determined when the correlation coefficient is equal to or smaller than a set value. When the value deviates from the normal value, it can be determined that the degree of stress becomes higher than that in the normal state due to, e.g., disturbance. With this processing, whether the degree of stress is normal or abnormal can be detected for each behavior.

Even in the following case, whether the degree of stress is normal or abnormal can be detected. For example, FIGS. 7A, 7B, and 7C are views showing displayed vital information/behavior display windows. As shown in FIG. 7A, a pulse rate trend graph is displayed on the monitor window every moment, indicating that the pulse rate abruptly increases during walking. Such an abrupt increase deviates from the normal pattern and can be determined as abnormality.

This pattern can be estimated as a running state (the user is running). Hence, as shown in FIG. 7B, a question window, "A change in measurement data is detected. You seem to be running, and the pulse rate is higher than usual. What is the matter with you?" is presented on the display panel, and the user is requested to answer the question. Answer examples such as "I'm running not to be late for work in the afternoon", "for training", and "being chased" are prepared and displayed, and the user is made to select one of them. If the user selects "I'm running not to be late for work in the afternoon", it can be determined that "the pulse rate has increased because the user is in a hurry", and consequently, it can be detected that "the degree of stress is + (plus)" (FIG. 7C). Even when the main module 101 executes such processing, whether the degree of stress is normal or abnormal can be detected for each behavior.

Next, to grasp the contents of the users feeling for the degree of stress, the user is asked about subjective information by speech dialogue (step S208 in GIG. 2). The dialogue structure of the speech dialogue used at this time is built by processing in the main module 101 in accordance with the users situation (step S209), or a dialogue structure stored in the past in the personal sensor information corpus DB2 serving as a material database is acquired together with sensor information. This will be described below in more detail.

<Dialogue Structure Acquisition Method>

A method of acquiring the dialogue structure from the sensor information corpus DB2 will be described with reference to FIG. 5. As shown in FIG. 5, the reference sensor information corpus DB2 has, in one record, environment (season, time, place, posture, action, behavior, and expected behavior), physical information (pulse rate, body temperature, GSR, and voice pitch), degree of stress, and dialogue structure. The similarity between the environment and physical information and the measurement data (vital information) obtained from the user is obtained, and the degree of stress is calculated using an evaluation function. A value equal to or larger than a certain reference value is recognized as a record that represents the user's situation, and the degree of stress and a dialogue structure for coping with the stress are acquired (step S210 in FIG. 2).

For the degree of stress determined (acquired from the average sensor information corpus), the user may be asked a question "You seem to be considerably tired", "You seem to be tired a little", or "Are you tired?" The degree of stress may be corrected for the user on the basis of an answer from the user, and the correction result may be reflected on the corpus DB2.

For example, assume that the pulse rate increases before a meeting. The system grasps this situation and asks the user a question "Your pulse rate is rising before meeting. Are you planning presentation?" The user returns to the system an answer "Yes, I have important presentation. I feel stressful". Upon receiving this answer, the system side gives an advice to the user to get rid of the stress, "Breathe deeply and relax, or how about something to drink?", and the user replies "OK".

Figure 6:
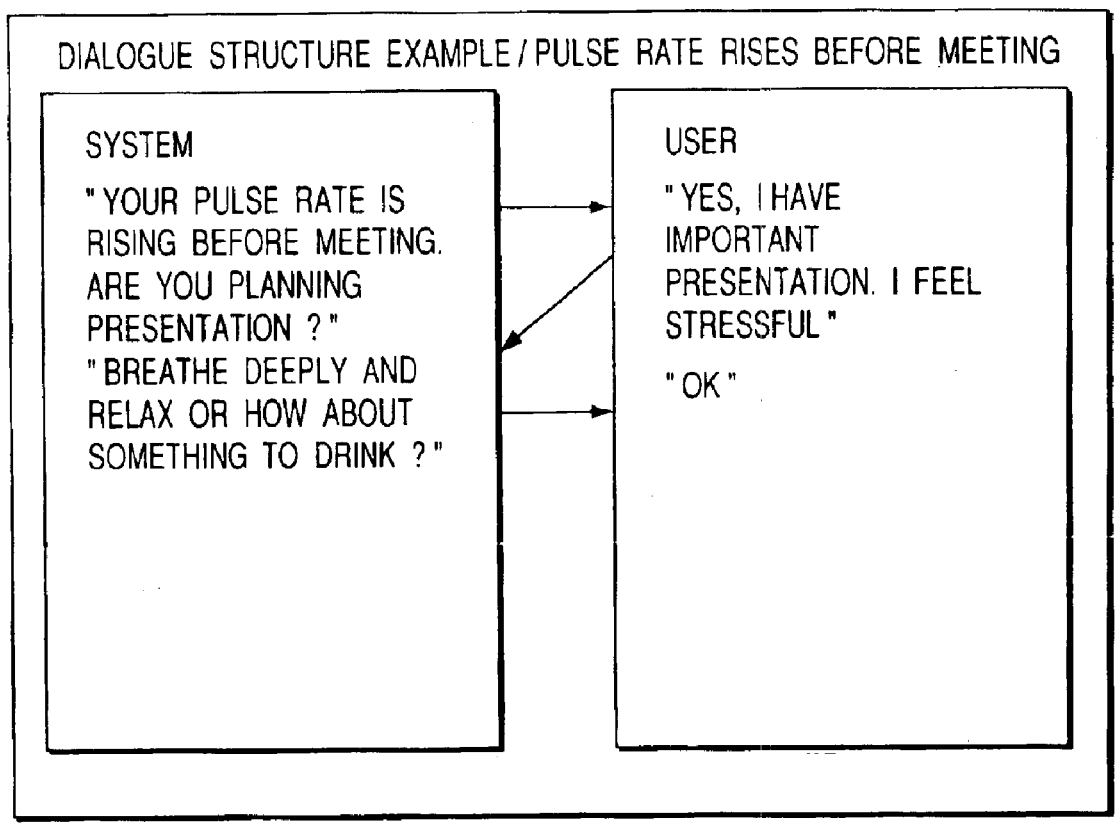
FIG. 6 is a view for explaining the dialogue structure for a situation registered in the sensor information corpus used in the embodiment of the present invention.

The main module 101 registers the dialogue result in the sensor information corpus DB2 as a dialogue structure for a specific situation by processing in the CPU 1012. In this example, a dialogue structure as shown in FIG. 6 is registered as a dialogue result. For a situation "dialogue structure: pulse rate rises before meeting", a dialogue structure for the situation is registered in the sensor information corpus DB2 with contents "System: "Your pulse rate is rising before meeting. Are you planning presentation?""→"User: "Yes, I have important presentation. I feel stressful""→"System: "Breathe deeply and relax or how about something to drink?""→"User: "OK""

The degree of stress may be detected by continuously analyzing the frequency component of the user's voice. As a characteristic feature of a human voice, the characteristic feature of the degree of stress appears in the frequency component and time-axis component of voice so that, for example, the frequency of the generated voice becomes higher than usual. On the basis of this fact, the degree of stress can be detected by continuously analyzing the frequency component of the user's voice during the dialogue. Hence, when the degree of stress is measured by voice frequency analysis, the degree of stress can be more accurately measured (step S211 in FIG. 2).

Alternatively, if the user feels difficulty (pressured) to speak with someone or one of participants of the current meeting, it is determined that the degree of stress is high. First, subjective data for that person is stored in the address book of the PIM software. The determination is done on the basis of vital information (pulse rate, GSR, and the like) when the user meets the person. If the pulse rate is high or the integrated value of GSR becomes large during speaking with that person, items "person (name)", "address", "telephone number", . . . , "degree of stress" are stored in the address book having a structure shown in FIG. 14 as data of a person for which the user feels stressful.

When the user meets the person, the person is recognized from the image or by inputting the name by voice recognition whereby the user's PIM data is obtained from the database DB1 to acquire the data of the degree of stress for that person. In addition, the emotion of the person is recognized from the speech and behavior of the person, the degree of stress is acquired even from the current vital information, and the degree of stress of the user is determined by combination of these data.

The degree of stress is set as frequency data, and the data are averaged every time the user meets that person. The expected degree of stress becomes high for a person for which the user habitually feels stressful.

Alternatively, the situation when the user meets a person (e.g., schedule information such as "ordinary meeting" is recorded in linkage with the degree of stress, and the degree of stress corresponding to each situation is stored in the corpus having a structure shown in FIG. 15. When schedule data in the future and participants (persons) are input, the expected degree of stress is calculated on the basis of a predetermined degree-of-stress formula, so the user is advised before the meeting to control the stress to some extent.

A person sometimes feels stressful depending on the distance from another person. This is understood as a concept "personal space". The distance changes even depending on the mental condition of a person. When the degree of stress by this concept is also measured, the degree of stress can be more practically reflected. More specifically, the distance from a person is measured using a distance sensor (e.g., an ultrasonic distance sensor or infrared distance sensor) attached to the user, recorded in association with the situation such as the name of the person and date/time/place. The personal space for each situation is also measured, and the degree of stress is counted for each situation in accordance with the person or the time while the person is in the personal space.

Another factor for stress build-up is a bad smell or strong smell. The intensity and kind of peripheral smell may be recorded using an odor sensor and converted into a degree of stress.

Still another factor for stress build-up is time. The degree of stress becomes high when the schedule is tight or when the user has a work with time limit. The degree of stress is linked with task (To-Do) data or an event of schedule and recorded, as shown in FIG. 15. As the time limit nears, it is determined that the degree of stress is high.

The schedule, task, and corresponding degree of stress are stored in the corpus shown in FIG. 15, which has items "season", "day of week", "schedule/task (To-Do)", "content/ volume", . . . , "degree of stress", and "degree of fatigue". The schedule and task are freely input. To search the corpus for an item name, keyword search is used, and the closest item is obtained in consideration of other situation data.

The degree of stress and subjective information of the user are acquired by the above device, deficient data are supplemented and corrected, and the subjective information is recorded (step S212 in FIG. 2). When the degree of stress is more than a predetermined threshold value, and it is determined that the user is stressed, the data of the degree of stress is transmitted to the information providing service agent together with the data of the user's situation, and an information providing service appropriate for the user is offered on the basis of the data (step S213 in FIG. 2). Potential service menus are 1. Distribution of music, image, and short-short story (relaxation)
2. Advice/navigation for event (to increase concentration)
3. Combined service of 1 and 2

The user is inquired about the service menu at the start time of use of the terminal (in this case, the start time of use of the main module 101 and the like) or when the main module 101 and the like are powered on. The user can set the service menu as he/she likes.

For the service contents, if the user selects, e.g., the relaxation course, and the user is stressed, a voice message "You seem to be tired. How about music? Please look at the display" is presented to the user, and a music list is displayed on the portable display such as the display 104 or wrist watch type display 105.

In this case, the system links to a content distribution service agent for music or the like, extracts optimum contents for the user from the database of the service agent on the basis of the data of the user's situation (where the user is and what the user is doing) and the data of the degree of stress (the degree of fatigue and whether the user is being stressed), and presents candidates to the user. When the user selects a content from the list, a confirmation message "Playback of this content costs \○○. OK?" is displayed. When the user inputs an acknowledge, the system buys and downloads the content and displays or plays back the stream of data. A questionnaire of the result is acquired and fed back to the database.

For the "advice/navigation for event" course, a service is offered to navigate the user such that the maximum efficiency can be obtained within the allowable range while allowing stress to some extent. Various kinds of events are prepared in accordance with the situation of each user. For example, "professional sports player", "amateur sports player", "examination", "presentation", and the like are prepared. When the date of actual event is set, the CPU 1012 of the main module 101 sets navigation menus from the service start day to the actual event and during the event and executes the service.

The menus may be continuously set in a scale with which relaxation can be obtained at maximum efficiency. In this case, break and relaxation necessary for maximizing the efficiency are provided. If the service mainly aims at eliminating stress, the amount of break and relaxation to be provided is increased.

The relaxation service is provided at a timing according to the measured user's situation. When the user is acting to have an effect on the target event or given task (e.g., during study for an examination), no relaxation service is provided. When the behavior continues, and the user starts feeling tired, the service is provided with relaxation advice. Alternatively, control may be performed such that a parameter that reflects a change in sympathetic and parasympathetic nerves, e.g., a fluctuation in heart rate, is measured, when the sympathetic nerve is active, an advice menu for maximizing efficiency under that situation is displayed, and when the parasympathetic nerve is active, the relaxation service is provided because a break is necessary.

Alternatively, since the control method changes depending on whether stress is preferred or undesirable for the user, the type of stress may be estimated from the user's situation, and a service according to the type of stress may be provided.

<Method of Determining Type of Stress>

The method of determining the type of stress will be described. Stress is detected by the method that was already described above. After that, indices that represent whether the stress is preferred or undesirable for the user are continuously expressed as numerical values, evaluated by the user, and stored in the personal sensor information corpus DB2. In the same situation, it is determined whether "navigation for eliminating the stress is to be performed" or "navigation for maximizing the ability is to be performed".

With the above processing, the type of stress can be determined, and how to reflect the stress on the service can be determined.

Figure 8B:
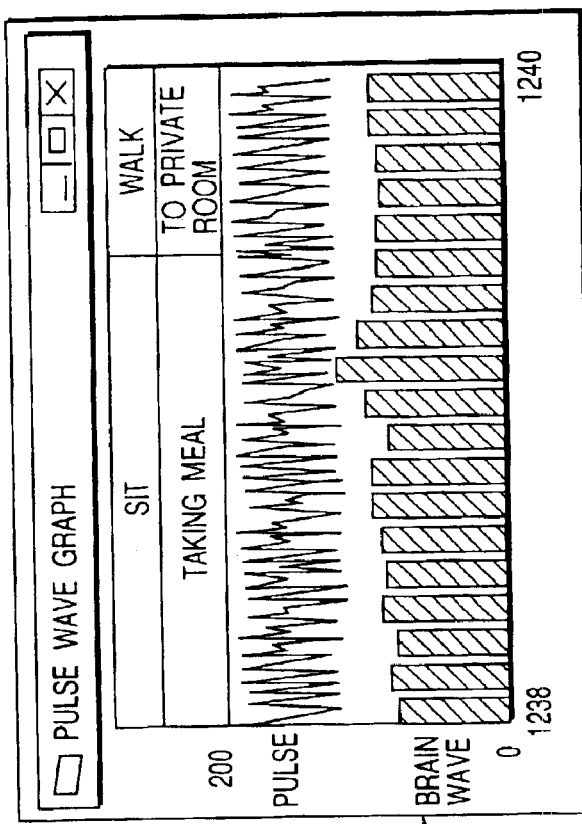
FIGS. 8A and 8B are views for explaining a display window of vital information related to a behavior, which is used in the embodiment of the present invention.
Figure 8A:
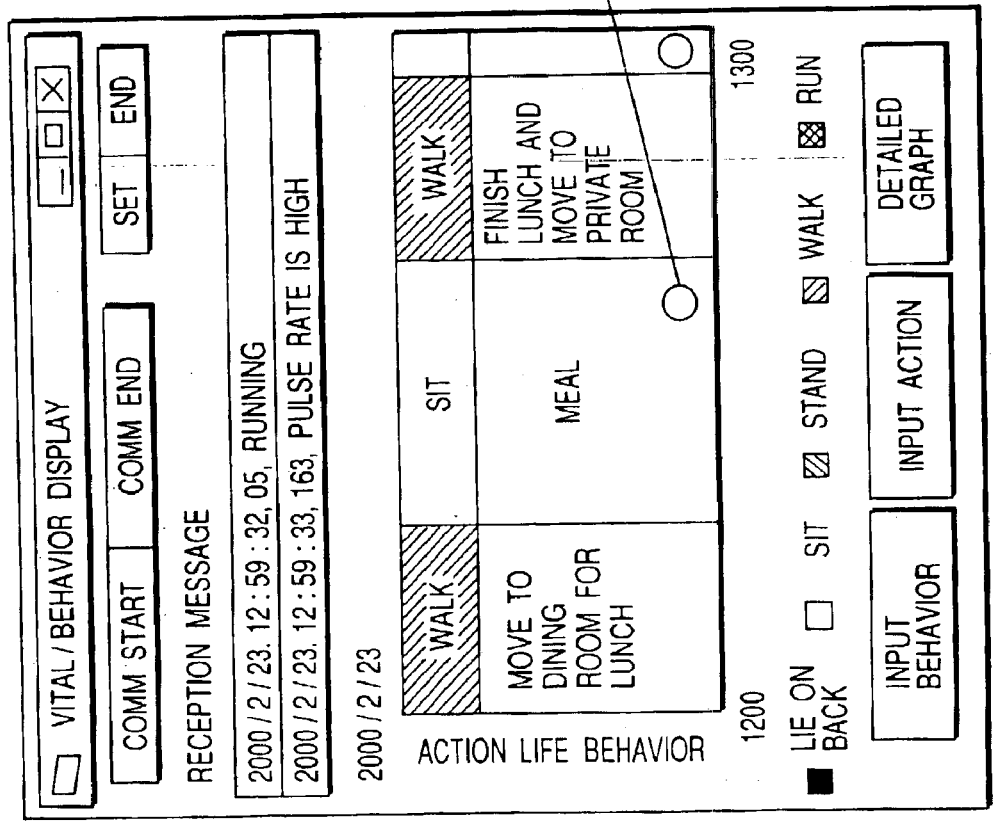

Since the vital information and behavior information of the user are always acquired, window information which allows the user to check the history for a predetermined past period from the current time may be generated on the basis of the monitor results of the vital information, posture/action information, and the like, sent to the terminal, and displayed on the user's display such that the user can refer to the history. In the example shown in FIG. 8A, action life information (in this example, [walk (walking)] move to dining room for lunch, [sit (sitting)] meal, [walk (walking)] finish lunch and move to private room) for a predetermined past period from the current time, or the current behavior state (running) and current physical condition (pulse rate is high) are displayed together with operation buttons and the like. In this example, when desired one of the pieces of displayed action life information is selected on the window, the graph of vital signals at that time is displayed, and the user can see the transition state (FIG. 8B). In this example, the vital signal graph shows the pulse wave and pulse rate, though any other vital signal can be displayed.

In the above first embodiment, pieces of vital information of the user, including the pulse rate, body temperature, and GSR, are acquired, and the posture information of the user is also acquired. A change in user's physical condition is detected from the pieces of information. When the pieces of information are collated with the behavior schedule of the user, and the change in user's body does not match the behavior schedule, the degree of stress is measured, and a service or advice for eliminating or relaxing the stress, or maximizing the ability by using the stress is provided to the user in accordance with the degree of stress and the user's situation.

Hence, a life support apparatus which can relax stress and suppress mental and physical damage by the stress to achieve effective medical administration and healthcare can be provided. In addition, a life support apparatus capable of increasing the ability by taking advantage of stress can be provided.

The second embodiment will be described next, in which when a user feels stressful, a measure recommended to the user can be commercially advertised to realize healthcare of the user and commercial effect, or pieces of information related to the stress are collected from the user and used for consulting or marketing business to effectively use the information for business.

(Second Embodiment)

In the second embodiment, in providing a service or presenting information, the physical and mental conditions of a user are always grasped, and an advertisement corresponding to the conditions is displayed through a wearable computer. The hardware configuration to be used is the same as that shown in the block diagram of FIG. 1.

The behavior information, vital information, and degree-of-stress information of the user are acquired by the same arrangement and method as in the first embodiment in the above-described way. After the pieces of information are acquired, an advertisement genre corresponding to the user's situation is estimated in a wearable computer (main module 101 in FIG. 1) on the basis of the acquired information, and data of the selected advertisement genre is transferred to an advertisement service agent.

As described above, the main module 101 has a Bluetooth chip 1013 for radio communication. As a network using Bluetooth is built, many radio tags (Bluetooth chips) as Bluetooth transmitting/receiving sections are installed at various places such as on a street, at a station, or in a building, and the main module 101 communicates with a radio tag, thereby communicating with the network. The server of an advertisement service agent is connected to the network. The server of the advertisement service agent distributes, through the network, advertisements corresponding to genre data sent from the main module 101 of the user. The advertisement distribution is done in a form of mail, voice message, banner on a display, or the like, and the advertisements are exchanged through the Bluetooth.

For advertisement distribution on the server side, optimum contents are provided and displayed on the device on the user side in accordance with the current situation of the user at the most effective timing for advertisement. For example, if the user is on his/her way to the office, an advertisement related to the work of the day is provided and displayed, as shown in FIGS. 11A and 11B. If the user is on his/her way to home, an advertisement related to hobby or articles for daily use including foods and clothes, or an advertisement of a supermarket near the route to home is provided and displayed before the purchase chance of the user is lost.

The display contents and display medium can be switched in accordance with the user's mental condition (whether the degree of stress is high or low). For example, when the degree of stress is high, and the user's mind is occupied with his/her own affairs, advertisement distribution is stopped. Advertisements are distributed later when the user is relaxed.

In the above description, the advertisement distribution agent selects contents to be distributed. However, the terminal side (wearable computer) may have a function of selecting an advertisement to be received and displayed in accordance with the situation of the user himself/herself. Alternatively, the server of the service agent may execute the filtering in accordance with setting information from the user and distribute advertisements.

Not only the contents to be displayed but also the display medium may be switched in accordance with the user's situation. For example, when it is recognized from behavior information that the user is walking, an advertisement to be provided is presented not by character and image data but by voice data.

As another example, personal behavior data and subjective information for the data may be collected and used for marketing/consulting business. Since the wearable computer (main module 101) stores personal behavior data and subjective information for the data, the agent acquires the pieces of information provided from the user. Since the pieces of information are personal information, they must be provided based on user's will. For this reason, the pieces of information are transmitted to the service side by transmission operation by the user himself/herself.

Figure 13A:
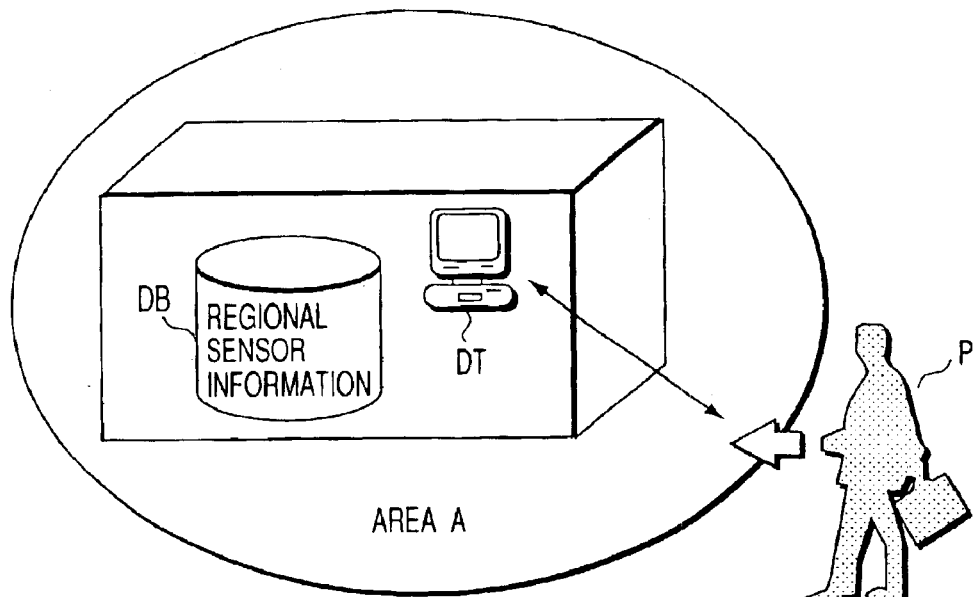
FIGS. 13A and 13B are a view and flow chart, respectively, showing collection of information of a person who passes by a convenience store and advertisement display, which are used in the embodiment of the present invention.

For a consulting service, the pieces of collected information must correspond to the consulting service to be provided. For example, for a consulting service to a convenience store, pieces of information must be collected from persons who have come to or near the convenience store. As shown in FIG. 13A, to collect data of a person P who has arrived at the neighborhood (area A) of the store, Bluetooth radio tags are installed at and near the store and connected to a person who has entered that area using the Bluetooth (step S1301 in FIG. 13B). When connection is successfully established, the system inquires of the person, presents the types and distribution destination of data, and obtains user's consent about whether the data may be sold (step S1302 in FIG. 13B).

Figure 13B:
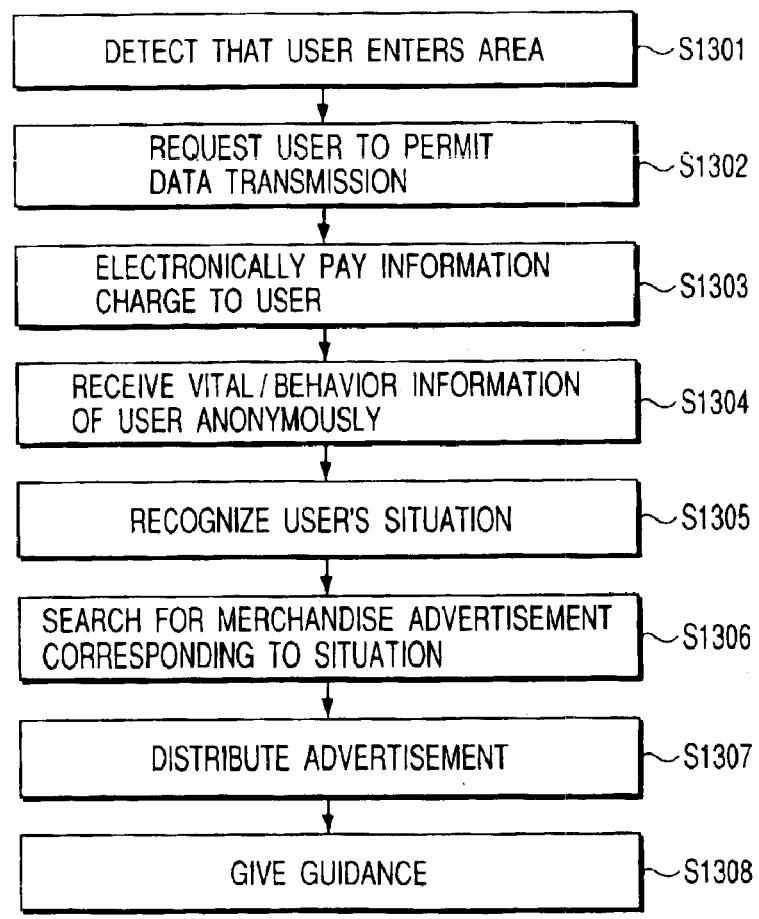

For easy data collection, an information charge is paid to the user who has communicated at that time, or a special coupon is offered to the user (step S1303 in FIG. 13B). In addition, to survey stores where the residents near the convenience stores buy, pieces of information of commercial areas familiar to the residents are collected. For the collected data, when only anonymous data is used, as shown in FIG. 12, and the user is informed that only anonymous data is used, the collected data can be sold as merchandise without any serious problem.

By collecting information in the above way, personal behavior data of many persons who live/work around the store and subjective stress information for the behavior data are collected, and therefore, the merchandise display contents at the convenience store can be easily optimized.

As described above, when a mechanism is built to collect data using the wearable computer capable of collecting pieces of information of behavior of a user and the information of the degree of stress caused by the behavior and collect the collected data in the server on the network using the Bluetooth, the data can be used for marketing and consulting services in terms of stress, e.g., the data can be reflected on the stock of pieces of merchandise which are useful to get rid of the stress or advertisement distribution for sales campaign in correspondence with the degree of stress of each person. For commercial use, since the statistic of persons who pass near a store can be acquired, and the actual conditions of consumers can be grasped, the merchandise display can be controlled for each time zone.

Conversely, when a person suitable to the merchandise display contents comes (steps S1304 and S1305 in FIG. 13B), the advertisements of the merchandise and store can be displayed (steps S1306 and S1307 in FIG. 13B). For example, when a person who happens to pass the store seems to be stressed (step S1305 in FIG. 13B), an advertisement that recommends a candy or food of his/her favorite is distributed (steps S1306 and S1307 in FIG. 13B) and displayed on the wearable computer of that person (step S1308 in FIG. 13B) to stimulate his/her will to buy. A system capable of promoting sale can be built and operated.

For such marketing survey, not only information at a specific point as described above but also information of a person near a surveyor may be collected by giving a wearable computer to the surveyor.

Another embodiment will be described below. For example, an agent that sells healthy foods lends or sells at a low price a wearable computer set as shown in FIG. 1 to a consumer. Using the wearable computer set, the behavior information, degree of stress, and health state of the user are measured by the above-described device.

The consumer (user) transmits the data of his/her own to the health advice service agent. The service agent receives the medical examination result. Alternatively, the pieces of information are periodically collected and automatically transmitted to the service agent, or the agent accesses the terminal of each user to collect information and determine the situation. It is determined whether the situation allows presentation of an answer to the user, and the examination result is transmitted from the system of the service agent using a medium according to the situation. The user side receives the transmitted examination result by the user's terminal.

Figure 9B:
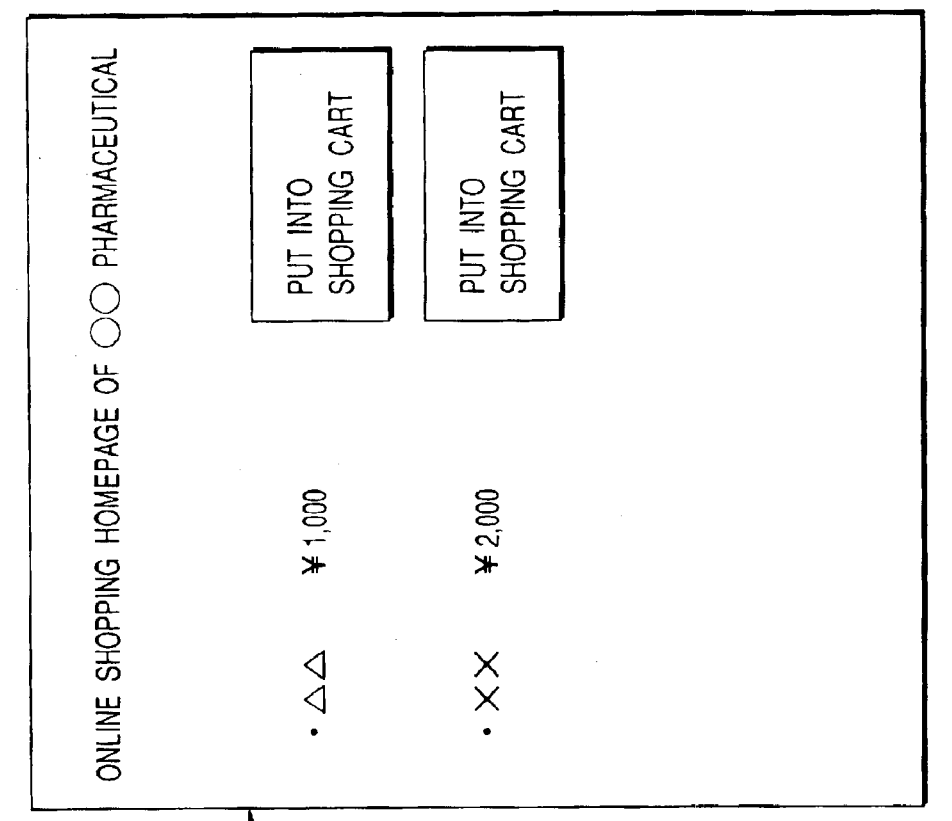
FIGS. 9A and 9B are views for explaining situation-dependent advertisement display and an online shopping window according to the display, which are used in the embodiment of the present invention.
Figure 9A:
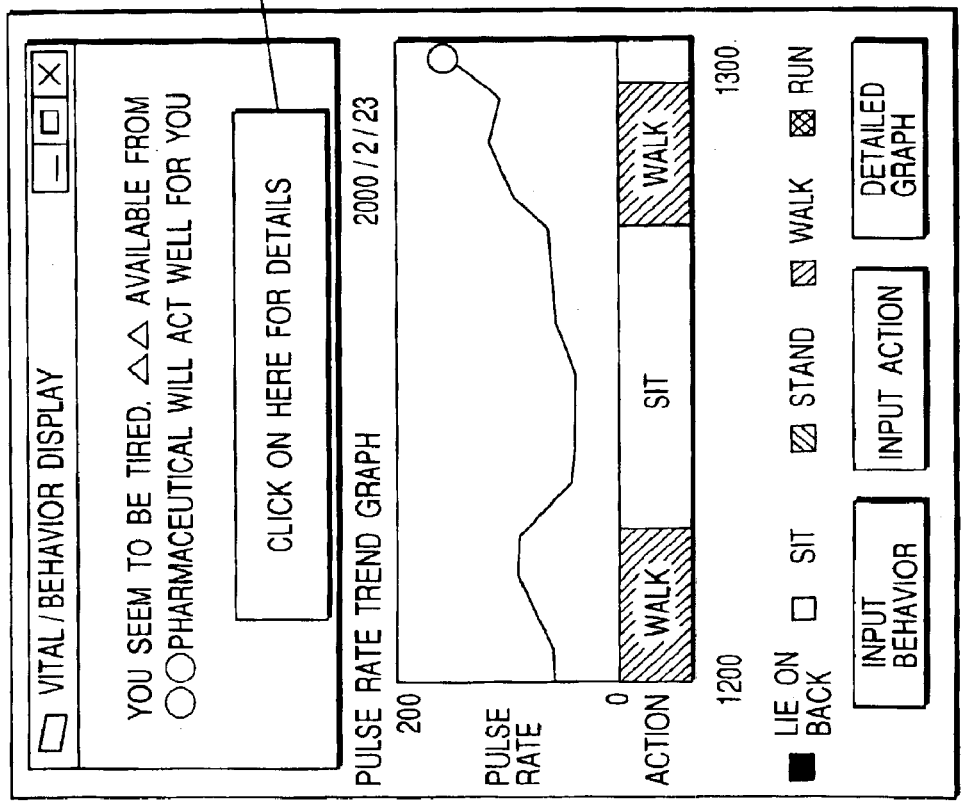

Simultaneously, a banner advertisement of a healthy food or medicine (FIGS. 9A and 10A) related to the examination result is displayed, or the homepage of an online shopping service is displayed (FIG. 9B). For example, for a user who feels tired, a banner advertisement or a page of online shopping, that recommends a vitamin C tablet or medicine for promoting nutrition, such as a nutritive drink, is displayed. To actively obtain the sales promotion effect, a coupon service is executed to offer "a point service for use of the service as a benefit" or "a special coupon (e.g., free drink ticket or the like) as a benefit". When the advertiser is a store, a store guide map display button is displayed on the banner advertisement (FIG. 10A). When the user operates this button, a map (FIG. 10B) for the store or a voice guidance (FIG. 10C) can be effectively given.

As described above, the life support apparatus according to the second embodiment uses a wearable computer having a Bluetooth as a short-distance radio communication device and a function of collecting vital information and behavior information. The user carries the apparatus and uses for his/her health care against stress. In addition, pieces of information for the stress are collected from a pedestrian to the server through a radio tag (e.g., a Bluetooth chip) on the street and network. When the user feels stressful, to eliminate the stress, a content for commercially advertising a measure recommended to the user is distributed to the user to keep him/her informed. With this arrangement, a system capable of realizing healthcare of the user and providing a commercial effect can be built. In addition, a system which can be effectively used for business by analyzing pieces of information of the behavior of a user and information related to stress, which are collected in the server, and using the information for consulting and marketing services can be built.

(Third Embodiment)

In the third embodiment, a life support apparatus which presents a user's situation acquired using the above user's situation recognition device by a means optimum for each inquiring medium in response to an external inquiry from a handyphone, mail, or beeper is provided.

In this embodiment as well, the hardware configuration is the same as in FIG. 1, and the behavior information, vital information, and degree-of-stress information of a user can be acquired by the same arrangement as in the first embodiment.

An example in which a real-time voice (telephone) message is received by a handyphone 107 will be described.

Figure 16:
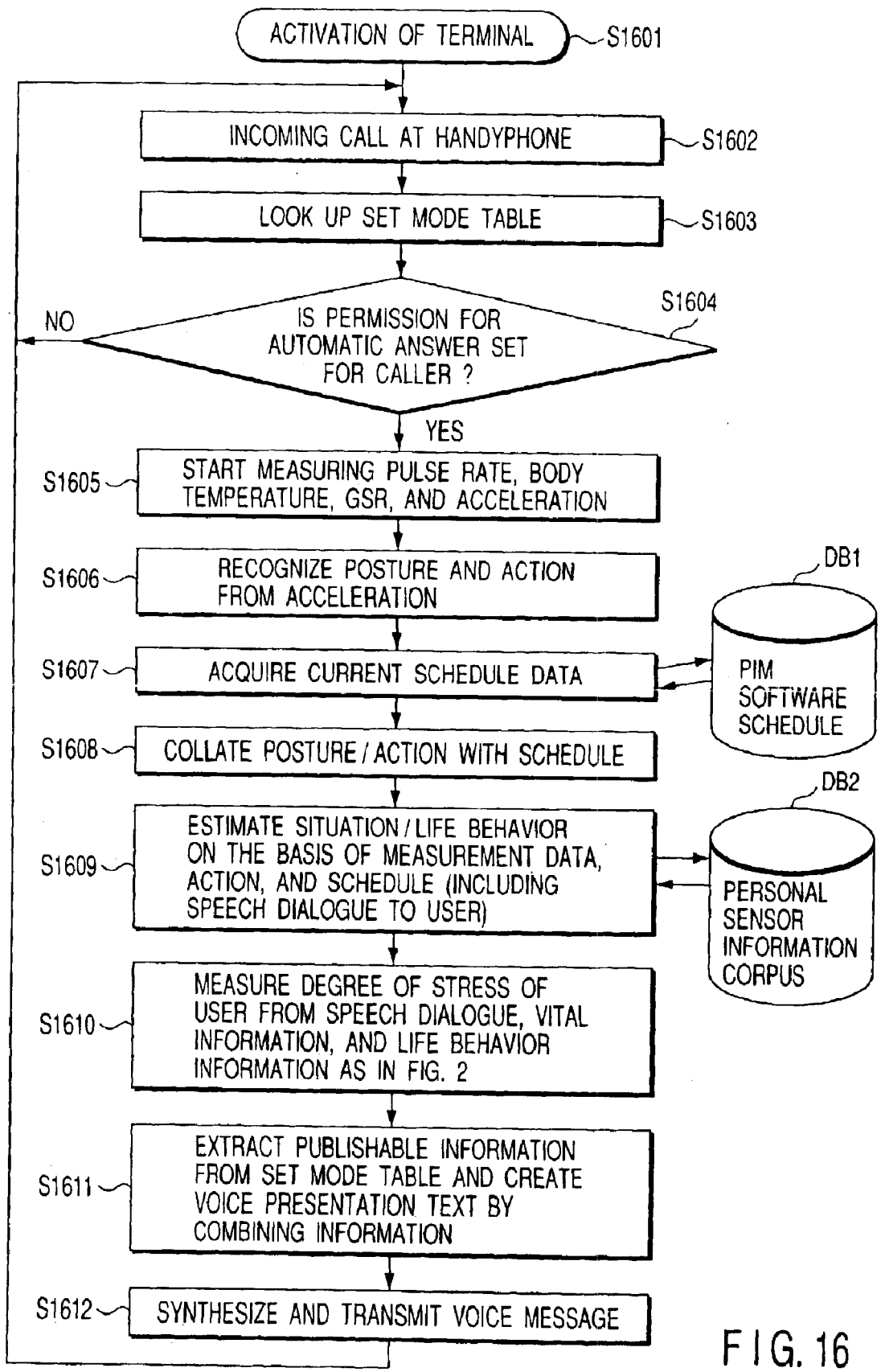
FIG. 16 is a flow chart of processing of returning a situation-dependent automatic answering telephone message to a handyphone according to the third embodiment of the present invention.

FIG. 16 is a flow chart showing the processing.

When a terminal (main module 101) is activated, the behavior information, vital information, and degree-of-stress information of the user are acquired by the main module 101 in accordance with the same arrangement and method as in the first embodiment. In case of an incoming call at the handyphone 107 (steps S1601 and S1602 in FIG. 16), a CPU 1012 of the main module 101 looks up a set mode table shown in FIG. 18 (step S1603 in FIG. 16).

In the set mode table shown in FIG. 18, information representing "whether an answer to an incoming call can be sent (YES/NO)", "the contents to be returned", "whether the fact is to transmitted", and the like can be set for each category of the caller and for each person. Several types of such table are stored in the handyphone 107 in advance. When the user selects and sets the table on the handyphone 107, the main module 101 can acquire and use the table information.

The CPU 1012 of the main module 101 starts user's situation recognition processing in accordance with the condition of the set mode table unless the answer is inhibited. Various data (vital information) collected by an acceleration sensor module 103 and sensor module 102 of the user are transmitted to the main module 101. The acceleration sensor module 103 includes a memory 1031, a CPU 1032, a Bluetooth chip 1033, and a preprocessor 1035. Upon receiving these data, the CPU 1012 of the main module 101 recognizes the users situation, as in the first and second embodiments, and accesses the handyphone 107 through the Bluetooth chip on the basis of the information. In other words, it is determined whether permission for automatic answer is set for a caller (S1604). If this determination is YES, measuring of a pulse rate, body temperature, GSR, and acceleration is started (S1605). The posture and action is recognized from the acceleration (S1606). Current schedule data is acquired (S1607). The posture and action are collated with the schedule (S1608). The situation and life behavior are estimated on the basis of measurement data, action and schedule (including speech dialogue to user) (S1609). The degree of stress of the user is measured from the speech dialogue, vital information and lifer behavior information as in FIG. 2(S1610). The CPU 1012 extracts publishable information from the set mode table incorporated in the handyphone 107 and creates voice presentation text by combining the information (step S1611 in FIG. 16).

For example, assume that it is determined that the user is on a train by situation recognition on the basis of information from the acceleration sensor module 103 and schedule, and that the user is in the section between Jiyugaoka and Nakameguro (Toyoko Line) from position information (for outdoors, the location is detected using the position information service of the handyphone (PHS) or a GPS (not shown)). According to the user's schedule, he/she is already waiting for a friend in Shibuya now, so text "I'm on the train, and will arrive at Shibuya in 10 minutes" is created. This text is synthesized into a voice message and returned to the caller as an answer from the handyphone (step S1612 in FIG. 16).

This text may be displayed on the handyphone of the user (callee), and a window for inquiring of the user about whether the answer can be transmitted may be displayed. When the user selects "YES", the answer is transmitted. This prevents the situation from being carelessly externally transmitted.

Figure 20:
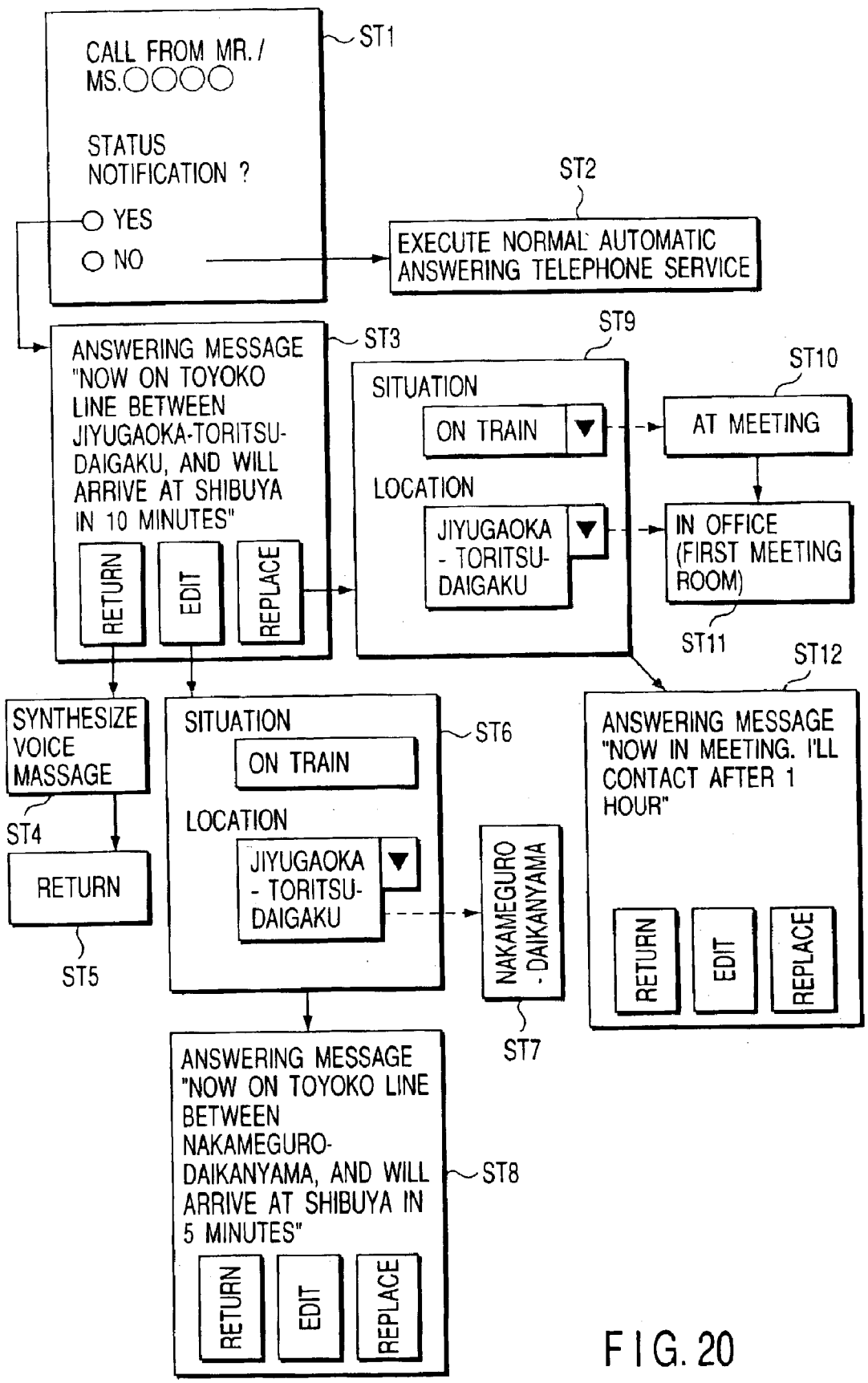
FIG. 20 is a view showing message display window transition that is used in the embodiment of the present invention.

Alternatively, upon reception of an incoming call, information such as the name of the caller is displayed on a portable display 104 or the display section of the handyphone 107, as shown in FIG. 20, and an answering message is selected and input on the window. For a notification medium, the table shown in FIG. 19 is set, and a notification is sent in accordance with the table.

The example of table shown in FIG. 19 has the following meaning. When the location is "outdoor", and the action is "walk", the incoming call notification is a "voice message", and a "voice message" is output for message display. When the location is "on train", and the action is "stand", the incoming call notification is done by "vibration", and message display is done by "text display on a wrist watch type display 105". When the location is "on train", and the behavior is "sit", the incoming call notification is done by "vibration", and message display is done by "display 104". When the location is "indoor", and the action is "—(arbitrary)", the incoming call notification is done by "vibration", and message display is "not performed".

If notification is to be executed in several steps, for example, the user is notified of only an incoming call by a voice message, and to display the contents as text, the user is notified of the medium or device where the details are to be displayed by a voice message.

When the notification is displayed on the display, and the use selects, e.g., "situation notification" (step ST1 in FIG. 20), the CPU 1012 of the main module 101 creates and displays notification text "I'm on the Toyoko Line between Jiyugaoka and Toritsu-daigaku. Will arrive at Shibuya in about 10 minutes" on the basis of situation information (step ST3 in FIG. 20). When the user checks the text and selects "transmit", the text is converted in accordance with the medium and transmitted to the caller (steps ST4 and ST5 in FIG. 20).

On the other hand, if the user selects "edit" in step ST3 of FIG. 20, a mode for editing the situation information is set (step ST6 in FIG. 20). In the edit mode, for example, "Jiyugaoka—Toritsu-daigaku" in the above example can be changed by the user to, e.g., "Nakameguro—Daikanyama" (step ST7 in FIG. 20). In accordance with this change, the CPU 1012 of the main module 101 automatically changes the message "10 minutes" as the required time for "Jiyugaoka—Toritsu-daigaku" to "5 minutes" as the required time for "Nakameguro—Daikanyama" (step ST8 in FIG. 20). This can be easily implemented by preparing a section required time table in advance, and when the section is changed in the edit mode, obtaining a corresponding required time by looking up the table.

When "replace" is selected in step ST3, the flow advances to step ST9 in FIG. 20 to allow whole message replacement, so any situation can be set. In this state, when, e.g., "in meeting" is selected (step ST10 in FIG. 20), text that represents that the user is in a meeting in the office can be created independently of the actual situation (steps ST11 and ST12 in FIG. 20). When the user checks the text and selects "transmit", the text is converted in accordance with the medium and transmitted to the caller the user does not select "situation notification" in step ST1, a normal automatic answering telephone service is executed (ST2).

The edit contents are changed in accordance with the user's situation and detectable range. For example, if "in meeting" is selected, the caller is notified of the time of end of meeting (the time of meeting is detected from the schedule).

When such edit operation cannot be performed because of the user's situation, the user is inquired by voice, or an answer is automatically sent in accordance with the conditions set in the table in advance.

As described above, the life support apparatus according to the third embodiment uses a wearable computer which has a Bluetooth as a short-distance radio communication device and also has a function of collecting vital information and behavior information, and can hold the user's schedule information and recognize the behavior state from that information. This apparatus grasps the behavior state of the user, and upon reception of an incoming call at the handyphone or the like, selects an optimum method of dealing with the incoming call from the current behavior state of the user. Even when an incoming call is detected on the train or during meeting, an optimum response method for that situation is automatically selected. For this reason, the user can respond to the caller without troubling those around the user. Hence, the user can optimally cope with termination of a call or mail without any stress.

Especially, for the conventional "manner" mode of a handyphone, when that the user cannot respond to the call can be presented to the caller together with the current situation, the caller can call the user again at a timing convenient for the user. This can be implemented by the third embodiment. In addition, an essential conflict of the conventional handyphone, i.e., the callee must answer the phone to explain that he/she cannot speak right now can be solved.

Various embodiments have been described above. In the embodiments of the present invention, information is presented to the user by voice synthesis. However, the present invention is not limited to this, and characters or image may be displayed on a head-mounted display (goggle type display), pendant-type display, or wrist watch type display. A wrist watch type display or handyphone may incorporate a vibrator. When a message for the user is received, the user may be notified of reception of the message by actuating the vibrator.

The feedback medium may be changed in accordance with the user's situation on the basis of the measured and recognized behavior. For example, when the user is walking, a voice message is output. During work, the message is displayed on the display window. When the user is sleeping, no message is output, though in case of emergency, those who are around the user are notified of the emergency as well as the user, or a message is transmitted to the family physician or security agent. In addition, the user may be notified of the emergency by strong vibration or voice to make him/her recognize the emergency level of the information.

When a state that the user cannot deal with is detected (when the user's disease is serious), a plurality of terminals in the neighborhood are notified of that state. In this case, many people in the neighborhood can recognize the emergency, and a system capable of quickly coping with emergency in the aged society or single aged household can be built. It is also useful to convert a message in accordance with the terminal to transmit information as to who is originating the emergency message and the place of origination, or to set emergency levels and, as the emergency level rises, alarm in a large volume.

If the user himself/herself must measure data (e.g., when automatic measurement or data transfer is impossible), a message for prompting the user to measure data is displayed in accordance with the measurement schedule. When no measurement is done, a follow message is periodically displayed. With this arrangement, the system can be prevented from irregularly functioning for a long time because no measurement result is obtained. The manner the message is displayed is preferably interactively adjusted.

In the above-described embodiments, the Bluetooth is used for communication between modules, though any other method can be used as long as communication at personal level is possible. A technique (PAN: Personal Area Network) of using a body as a conductor and exchanging an electrical signal has also been developed. Communication between modules may be executed using this technique. IrDA (infrared communication interface) can also be used. In the embodiments, communication between modules is executed as radio communication. However, cable connection may be performed using, e.g., RS232C as one of standard interfaces for serial communication.

As the transfer condition, pieces of vital information before and after a change in action may be transferred, the transfer rate may be raised (the priority level may be increased), or time resolving power may be increased. For example, when it is determined that the degree of physical action is high on the basis of the output from the acceleration sensor, or for a behavior for which considerable stress is expected by the above-described stress detection algorithm, the time resolving power for data to be measured is increased, and otherwise, the data are transferred at a low resolving power. The type of acquired information may be controlled. For example, an electrocardiogram is acquired in a high load state, and only a pulse rate is acquired in a low load state.

In an arrangement in which the sensor modules and main module have attached sensors, respectively, and sensors for acquiring the same data are also prepared on the environment side, wearable sensor modules may be used to acquire data when the sensors are attached, and the sensors on the environment side may be used to acquire data when the sensors are detached.

To implement this system, e.g., an energization type attached/detached status detection sensor in a sensor module is attached to the user. If the sensor is a potential or resistance detection sensor, that the sensor is detached is detected when the resistance is infinite or the electrodes are open, or a check signal is transmitted from the main module to repeat detection. That the sensor is detached is detected when no check signal is received. If the sensor is detached, the main module searches for a sensor capable of acquiring vital information and environmental information of the user from the environmental network, and if a sensor is found, the main module connects to the sensor to acquire data. If no sensor is found, a message "no sensor" is presented to the user and recorded in data together with the reason. For, e.g., the pulse sensor, when the user is taking a bath, the data is switched to the pulse rate from the electrocardiogram obtained while the user is in the bathtub. When the user is sleeping, data is received as an electrocardiogram from an electrode attached to the bedclothes, or a variation is detected by variation in breath (detected from an image).

In measuring on the environment side, if the communication state with the wearable device degrades, data are stored on the network side. When the connection state recovers, the data are transmitted to the wearable device. However, if an emergency occurs for the user, an alarm is directly output.

In the embodiments, measurement data is A/D-converted, and the situation is determined on the basis of a digital signal. However, this processing may be executed using an analog signal.

As described above, according to the present invention, it is an object of the present invention to provide a life support apparatus and method which can determine the stress situation in daily life and notify a user of it to cause the user to realize the stress or can support the user of a method of eliminating stress or care against the factor that has caused the stress, on the basis of the situation of the user.

Also, it is an object of the present invention to provide a life support apparatus and method which can determine the stress situation in daily life and, on the basis of the situation, provide a user optimum service information for stress elimination or care on the basis of the situation in consideration of specific time and circumstances, and prompt the user to use the service information, thereby contributing to the commercial effect and healthcare of the user.

Today, handyphones and the like show wide proliferation, and such a portable type communication device is one of necessary articles that a person cannot dispense with because of convenience that allows contact and communication anytime and anywhere. However, an incoming call at such a portable type communication device may trouble those around the user depending on user's situation, so the user must cope with the incoming call with constraint. This causes stress on the user, and therefore, must be solved.

Further, it is an object of the present invention to provide a life support apparatus and method which allow a user to select an optimum method of dealing with an incoming call at a handyphone or the like on the basis of the current behavior of the user, and also allow the user to automatically select an optimum method of responding to an incoming call even in a train or during meeting, thereby making it possible to optimally cope with an incoming call without troubling those around the user and also preventing the user from allowing stress to build up in.

As has been described above, according to the present invention, in a wearable type life support apparatus, the degree of stress is grasped without troubling the user on the basis of actual user's behavior history and vital information in accordance with the motion information measured from the user and schedule data, thereby navigating user's life in a desired direction, e.g., relaxing the stress or making it possible to perform operation at the maximum efficiency. When the pieces of information are collected in units of regions, they can be used for marketing in each region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A life supporting method comprising:

measuring vital information of a user using a vital information sensor;

generating behavior information of the user;

recognizing a user's situation based on the behavior information and the vital information to generate user's situation information;

storing, in a database, stress management information prepared in advance;

searching the database for stress management information corresponding to the user's situation information;

presenting searched stress management information to the user;

controlling a measurement condition of the vital information sensor in accordance with the user's situation information;

determining presentation contents and procedure to be presented as the stress management information;

searching the database for relaxation information for eliminating stress and navigation information for controlling stress and increasing an operation efficiency; and providing the relaxation information and navigation information in accordance with the user's situation and the presentation contents and procedure.

2. The method according to claim 1, wherein searching the database for the stress management information includes generating the stress management information useful for improving the user's situation.

3. The method according to claim 2, further comprising providing the stress management information in accordance with the user's situation and the presentation contents and procedure.

4. The method according to claim 3, wherein the stress management information includes information of a schedule and task of the user.

5. The method according to claim 3, wherein the stress management information includes a fluctuation of a sympathetic and a parasympathetic nature.

* * * * *